(12) United States Patent
Beaumont et al.

(10) Patent No.: US 9,273,118 B2
(45) Date of Patent: Mar. 1, 2016

(54) MEANS AND METHODS FOR PRODUCING HIGH AFFINITY ANTIBODIES

(75) Inventors: Tim Beaumont, Ouderkerk a/d Amstel (NL); Hergen Spits, Amsterdam (NL); Mark J. Kwakkenbos, Amsterdam (NL); Adrianus Q. Bakker, Hoorn (NL)

(73) Assignee: AIMM THERAPEUTICS B.V., Amsterdam (NL)

( * ) Notice: Subject to any disclaimer, the term of this patent is extended or adjusted under 35 U.S.C. 154(b) by 0 days.

(21) Appl. No.: 13/383,832

(22) PCT Filed: Jul. 15, 2010

(86) PCT No.: PCT/NL2010/050458
§ 371 (c)(1),
(2), (4) Date: Jan. 31, 2012

(87) PCT Pub. No.: WO2011/008093
PCT Pub. Date: Jan. 20, 2011

(65) Prior Publication Data
US 2012/0157662 A1    Jun. 21, 2012

Related U.S. Application Data

(60) Provisional application No. 61/225,882, filed on Jul. 15, 2009.

(30) Foreign Application Priority Data

Jul. 15, 2009   (EP) ..................... 09165603

(51) Int. Cl.
| | | |
|---|---|---|
| A61K 38/00 | (2006.01) |
| C12N 5/00 | (2006.01) |
| C07K 16/00 | (2006.01) |
| C07K 16/10 | (2006.01) |

(52) U.S. Cl.
CPC ............. *C07K 16/00* (2013.01); *C07K 16/1027* (2013.01); *C07K 2317/24* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,997,764 | A | 3/1991 | Dalla Favera |
| 5,684,147 | A | 11/1997 | Agrawal et al. |
| 5,849,900 | A | 12/1998 | Moelling |
| 5,866,757 | A | 2/1999 | Reisner et al. |
| 6,001,558 | A | 12/1999 | Backus et al. |
| 7,378,276 | B2 | 5/2008 | Ettinger et al. |
| 7,964,406 | B2 | 6/2011 | Spits et al. |
| 8,247,228 | B2 * | 8/2012 | Ettinger et al. ............... 435/377 |
| 2003/0099613 | A1 | 5/2003 | Berkhout et al. |
| 2003/0152559 | A1 | 8/2003 | Yang et al. |
| 2003/0158131 | A1 | 8/2003 | Aldovini |
| 2005/0009180 | A1 | 1/2005 | Yang et al. |
| 2005/0238626 | A1 | 10/2005 | Yang et al. |
| 2008/0274991 | A1 | 11/2008 | Berkhout et al. |
| 2008/0293068 | A1 * | 11/2008 | Tsien et al. ....................... 435/6 |
| 2008/0305076 | A1 | 12/2008 | Ettinger |
| 2009/0093024 | A1 | 4/2009 | Bowers et al. |
| 2009/0217403 | A1 | 8/2009 | Spits |
| 2010/0093038 | A1 | 4/2010 | Spits |
| 2010/0113745 | A1 | 5/2010 | Spits et al. |
| 2012/0070446 | A1 | 3/2012 | Beaumont et al. |
| 2012/0151613 | A1 * | 6/2012 | Wang et al. ..................... 800/14 |

FOREIGN PATENT DOCUMENTS

| | | |
|---|---|---|
| EP | 1 627 563 | 2/2006 |
| GB | 2 398 783 | 9/2004 |
| WO | WO 89/08146 | 9/1989 |
| WO | WO 94/08004 | 4/1994 |
| WO | WO 94/17086 | 8/1994 |
| WO | WO 95/06409 | 3/1995 |
| WO | WO 96/01313 | 1/1996 |
| WO | WO 01/20013 | 3/2001 |
| WO | WO 03/050262 | 6/2003 |
| WO | WO 03/052083 | 6/2003 |
| WO | WO 03/070193 | 8/2003 |
| WO | WO 03/079757 | 10/2003 |
| WO | WO 2005/052164 | 6/2005 |
| WO | WO 2005/102383 | 11/2005 |
| WO | WO 2005/123923 | 12/2005 |
| WO | WO 2006/016808 | 2/2006 |
| WO | WO 2006/132524 | 12/2006 |
| WO | WO 2007/058527 | 5/2007 |
| WO | WO 2007/067032 A1 | 6/2007 |
| WO | WO 2007/067046 | 6/2007 |
| WO | WO 2008/147196 | 12/2008 |
| WO | WO 2011/008093 | 1/2011 |

OTHER PUBLICATIONS

Kriangkum et al ., Blood, 2006,v.107, pp. 2920-2927).*
PCT International Preliminary Report on Patentability, PCT/US2010/050458, dated Sep. 27, 2011.
Alajez, et al., Therapeutic potential of a tumor-specific, MHC-unrestricted T-cell receptor expressed on effector cells of the innate and the adaptive immune system through bone marrow transduction and immune reconstitution; Blood, Jun. 15, 2005, vol. 105, No. 12; pp. 4583-4589.
Chlewicki, et al., High-affinity, Peptide-specific T Cell Receptors can be Generated by Mutations in CDRl, CDR2 or CDR3; J. Mol. Biol.; 2005; 346, 223-239.
Clay, et al., Efficient Transfer of a Tumor Antigen-Reactive TCR to Human Peripheral Blood Lymphocytes Confers Anti-Tumor Reactivity, Journal of Immunology, 1999, pp. 507-13, vol. 163, The Williams and Wilkins Co. Baltimore, MD, US.

(Continued)

*Primary Examiner* — Michail Belyavskyi
(74) *Attorney, Agent, or Firm* — Gianna Julian-Arnold; Saul Ewing LLP

(57) ABSTRACT

The invention provides means and methods for modulating the occurrence of somatic hypermutations in antibody producing plasmablast-like B-cells.

7 Claims, 14 Drawing Sheets

(56) References Cited

OTHER PUBLICATIONS

Figure 1A:
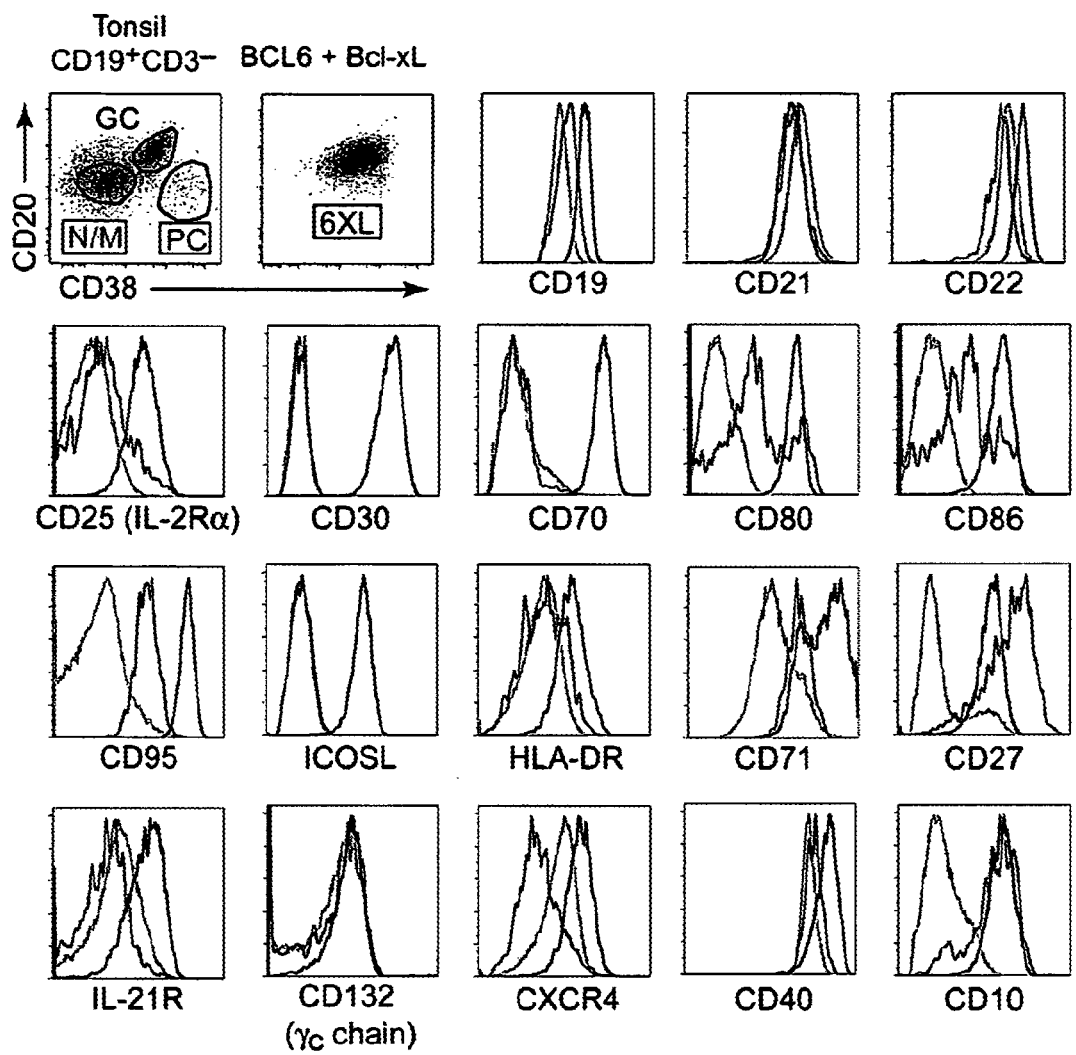

Clay, et al. Potential Use of T Cell Receptor Genes to Modify Hematopoietic Stem Cells for the Gene Therapy of Cancer, Pathology Oncology Research, 1999, pp. 3-15, vol. 5, No. 1, Budapest, Hungary.

Das, et al., Abstract, A Conditionally Replicating Virus as a Novel Approach Toward an HIV Vaccine, Methods in Enzymology, 2004, pp. 359-79, vol. 388, Academic Press, San Diego, US.

Das, et al., Viral evolution as a tool to improve the tetracycline-regulated gene expression system, The Journal of Biological Chemistry, Apr. 30, 2004, pp. 18776-18782, vol. 279, No. 18.

Gimeno, et al. Monitoring the effect of gene silencing by RNA interference in human DC34<+> cells injected into newborn RAG2<−/−> |gamma|c <−/−> mice: Functional inactivation of p53 in developing T cells, Blood Dec. 15, 2004 United States, vol. 104 No. 13, Dec. 15, 2004, pp. 3886-3893, XP002317351, ISSN: 0006-4971, the whole document.

Goldman, et al., Enhanced human cell engraftment in mice deficient in RAG2 and the common cytokine receptor gamma chain, British Journal of Haematology, Oxford, GB, vol. 103, No. 2, Nov. 1998, pp. 335-342, XP002249529; ISSN: 0007-1048, the whole document.

Gossen, et al., Abstract, Transcriptional Activation by Tetracyclines in Mammalian Cells, Science, Jun. 23, 1995, pp. 1766-1769, vol. 268, American Association for the Advancement of Science, US.

Kang, et al. Long-term expression of a T-cell receptor beta-chain gene in mice reconstituted with retrovirus-infected hematopoietic stem cells, Proc. Natl. Acad. Sci., Dec. 1990, pp. 9803-9807, vol. 87, National Academy of Science, Washington, DC, US.

Knott, et al., Tetracycline-dependent Gene Regulation: Combinations of Transregulators Yield of a Variety of Expression Windows, Biotechniques, 2002, pp. 796-806, vol. 32, No. 4; Informa Life Sciences Publishing, Westborough, MA, US.

Kobayashi, et al., Abstract, Prevention of acute liver failure in rats with reversibly immortalized human hepatocytes; Science (Washington, DC), vol. 287, No. 5456, Feb. 18, 2000, pp. 1258-1262, XP002159501, ISSN: 0036-8075.

Krueger, et al., Single-chain Tet Transregulators, Nucleic Acids Research Jun. 15, 2003, pp. 3050-3056, vol. 31, No. 12 Oxford University Press, Surrey, GB.

Kyba, et al. Enhanced hematopietic differentiation of embryonic stem cells conditionally expressing Stat5; PNAS, 2003, vol. 100, pp. 1-12.

Mathas et al., Intrinsic inhibition of transcription factor E2A by HLH proteins ABF-1 and Id2 mediates reprogramming of neoplastic B cells in Hodgkin lymphoma, Nature Inununology, Feb. 2006, pp. 207-15, vol. 7, No. 2.

Mulloy, et al. Maintaining the self-renewal and differentiation potential of human CD34+ hematopoietic cells using a single genetic element, Blood, vol. 102, No. 13, 15 Dec. 2003, pp. 4369-4376, XP002317905, ISSN: 0006-4971, the whole document.

Mehta, et al., IL-21 induces the apoptosis of resting and activated primary B cells, Journal of Immunology, Apr. 15, 2003, pp. 4111-4118, vol. 170, No. 8, The Williams and Wilkins Co., Baltimore US.

Office Action for U.S. Appl. No. 12/086,328 dated Oct. 21, 2011.
Office Action for U.S. Appl. No. 12/086,328 dated Feb. 22, 2012.
Advisory Action for U.S. Appl. No. 12/086,328 dated May 31, 2012.
Office Action for U.S. Appl. No. 12/085,107 dated Jun. 28, 2012.
Office Action for U.S. Appl. No. 12/086,269 dated Oct. 25, 2011.
Office Action for U.S. Appl. No. 12/086,269 dated Feb. 7, 2012.
Advisory Action for U.S. Appl. No. 12/086,269 dated May 24, 2012.
PCT International Search Report, PCT/NL2005/000739, dated Nov. 29, 2006.
PCT International Search Report, PCT/NL2005/000848, dated Jul. 10, 2006.
PCT International Search Report, PCT/NL2006/000277, dated Sep. 1, 2006.
PCT International Search Report, PCT/NL2006/000575, dated Jul. 27, 2007.

Petrie, et al., T Cell Receptor Gene Recombination Patterns, and Mechanisms: Cell Death, Rescue, and T Cell Production, J Exp Med 1995; 182: 121-7.

Salucci, et al., Tight control of gene expression by a helper-dependent adenovirus vector carrying the rtTA2S-M2 tetracycline transactivator and repressor systems, Gene Therapy, 2002, pp. 1415-21, vol. 9, Macmillam Press Ltd., Basingstoke, GB.

Schaft, et al.; Peptide fine specificity of anti-glycoprotein 100 CTL is preserved following transfer of engineered TCRαβ genes into primary human T lymphocytes; The Journal of Immunology, 2003, 170: pp. 2186-2194.

Schuringa, et al., Constitutive activation of STAT5A promotes human hematopoietic stem cell self-renewal and erythroid differentiation, Journal of Experimental Medicine, vol. 200, No. 5, Sep. 6, 2004, pp. 623-635, XP002317907, ISSN: 0022-1007.

Schuringa, et al.; Enforced Activation of STAT5A Facilitates the Generation of Embryonic Stem-Derived Hematopoietic Stem Cells That Contribute to Hematopoiesis In Vivo; Stem Cells 2004; 22: 1191-1204.

Shen Chun-Pyn, et al., B-cell-specific DNA binding by an E47 homodimer, Molecular and Cellular Biology, 1995, pp. 4518-4524, vol. 15, No. 8.

Stier, et al., Notch1 activation increases hematopoietic stem cell self-renewal in vivo and favors lymphoid over myeloid lineage outcome, Blood, vol. 99, No. 7, Apr. 1, 2002, pp. 2369-2378, XP002317904, ISSN: 006-4971, p. 2375, left-hand col.

Traggiai, et al., Abstract; Development of a human adaptive immune system in cord blood cell-transplanted mice; Science (Washington, DC) vol. 304, No. 5667, Apr. 2, 2004, pp. 104-107, XP002356076, ISSN: 0036-8075, the whole document.

Urlinger, et al., Exploring the sequence space for the tetracycline-dependent transcriptional activators: novel mutations yield expanded range and sensitivity, Proceedings of the National Academy of Sciences of USA, pp. 7963-7968, Jul. 5, 2000, vol. 97, No. 14, National Academy of Science, Washington, DC, US.

Vickers, et al., Efficient reduction of target RNAs by small interfering RNA and RNase H-dependent antisense agents, 2003, The Journal of Biological Chemistry, vol. 278, pp. 7108-7118.

Weijer, et al., Intrathymic and extrathymic development of human plasmacytoid dendritic cell precursors in vivo; Blood, 2002; 99; 2752-2759.

Yamochi, et al. Adenovirus-mediated high expression of BCL-6 CV-1 cells induces apoptotic cell death accompanied by down-regulation of BCL-2 and BCL-XL, Oncogene, Jan. 14, 1999, pp. 487-94, vol. 18, No. 2.

Yang, et al. Generation of Functional antigen-specific T Cells in defined genetic backgrounds by retrovirus-mediated expression of TCR cDNAs in hematopoietic precursor cells, Proceedings of the National Academy of Sciences of USA, Apr. 30, 2002, pp. 6204-6209, vol. 99, No. 9, National Academy of Science, Washington, DC, US.

Yang, et al., Long-tenn in vivo provision of antigen-specific T cell inununity by programming hematopoietic stem cells, Proceedings of the National Academy of Sciences of USA, Mar. 22, 2005, pp. 4518-4523, vol. 102, National Academy of Science, Washington, DC, US.

Zhou, et al., Improved single-chain transactivators of the Tet-On gene expression system, Biotechnology, 2007, p. 6, vol. 7.

Zhou, et al., Modification of the Tet-On regulatory system prevents the conditional-live HIV-1 variant from losing doxycycline-control, Retrovirology, 2006, p. 82, vol. 3.

Zhou, et al., Optimization of the Tet-On system for regulated gene expression through viral evolution, Gene Therapy, Oct. 2006, pp. 1382-90, vol. 13, No. 19.

Zhou, et al., the genetic stability of a conditional live HIB-1 variant can be improved by mutations in the Tet-On regulatory system that restrain evolution, The Journal of Biological Chemistry, Jun. 23, 2006, pp. 17084-17091, vol. 281, No. 25.

Shapiro-Shelef et al., Blimp-1 is required for maintenance of long-lived plasma cells in the bone marrow, The Journal of Experimental Medicine, Dec. 5, 2005, pp. 1471-76, vol. 202, No. 11.

(56) References Cited

OTHER PUBLICATIONS

Knodel, et al., Abstract, Blimp-1 over-expression abrogates IL-4-and CD40-mediated suppression of terminal B cell differentiation but arrests isotype switching, European Journal of Immunology, 2001, pp. 1972-1980, vol. 31, No. 7.

Ozaki, et al., Regulation of B cell differentiation and plasma cell generation by IL-21, a novel inducer of Blimp-1 and Bcl-6, Journal of Immunology, Nov. 1, 2004, pp. 5361-5371, vol. 173, No. 9.

Schvarts, et al., A senescence rescue screen identifies BCL6 as an inhibitor of anti-proliferative p19ARF-p53 signaling, Genes and Development, Mar. 15, 2002, pp. 681-86, vol. 16, No. 6.

Shaffer, et al., Blimp-1 orchestrates plasma cell differentiation by extinguishing the mature B cell gene expression program, Immunity, Jul. 2002, pp. 51-62, vol. 17, No. 1.

Traggiai, et al., Abstract; An efficient method to make human monoclonal antibodies from memory B cells: potent neutralization of SARS conoranavirus, Nature Medicine, Aug. 2004, pp. 871-75, vol. 10, No. 8.

Tosato et al., Identification of Interleukin-6 as an Autocrine Growth Factor for Epstein-Barr Virus-Immortalized B Cells, Journal of Virology, Jun. 1990, pp. 3033-3041, vol. 64, No. 6.

Koff, Vaccine vol. 30 (2012) pp. 4310-4315.

Vanregenmortel, Arch. Virol. vol. 157 (2012) pp. 1-20.

Toyama et al., Memory B Cells Without Somatic Hypermutation Are Generated From Bcl6-Deficient B Cells, Immunity, Sep. 1, 2002, pp. 329-339, vol. 17, No. 3, Cell Press, US.

Gil et al., Somatic Mutations and Activation-Induced Cytidine Deaminase (AID) Expression in Established Rheumatoid Factor-Producing Lymphoblastoid Cell Line, Molecular Immunology, Jan. 1, 2007, pp. 494-505, vol. 44, No. 4, Pergamon, GB.

Epeldegui et al., Infection of Human B Cells with Epstein-Barr Virus Results in the Expression of Somatic Hypermutation-Inducing Molecules and in the Accrual of Oncogene Mutations, Molecular Immunology, Feb. 1, 2007, vol. 44, No. 5, Pergamon, GB.

Muramatsu et al., Class Switch Recombination and Hypermutation Require Activation-Induced Cytidine Deaminase (AID), a Potential RNA Editing Enzyme, Cell, Sep. 1, 2000, pp. 553-63, vol. 102, No. 5.

Roughan et al., The Intersection of Epstein-Barr Virus with the Germinal Center, Journal of Virology, Apr. 15, 2009, pp. 3968-3976, vol. 83, No. 8, The American Society for Microbiology, US.

Tan et al., Zinc-finger Protein-Targeted Gene Fegulation: Genomewide Single-Gene Specificity, Proceedings of the National Academy of Sciences of the United States of America, Oct. 14, 2003, vol. 100, No. 21, pp. 11997-12002.

Lee et al., Regulation of the Germinal Center Gene Program by Interferon (IFN) Regulatory Factor 8/IFN Consensus Sequence-Binding Protein, Journal of Experimental Medicine, Jan. 2006, pp. 63-72, vol. 203, No. 1.

PCT International Search Report, PCT/NL2010/050458, dated Aug. 30, 2010.

* cited by examiner

— Bcl6 + Bcl-xL transduced cells (6XL, Black line)
Tonsil naïve and memory cells (N/M, Light gray line)
═ Tonsil plasma cells (PC, Dark gray line)
Tonsil germinal center cells (GC, Filled histogram)

FIG. 2a

FIG. 2a, cont'd

```
NON-BINDERS:
#58   ------------------------Y----------------------T-------P--A----------I
#70   ------------K-----------------------------------K--------------L------
#77   ---------------------------------------V--------K----------------------
#78   ---------------------------------------L--------K----------------------
#129  ----------------------------------V-------------K----------------------
#141  ------K---------------R-------------------------K----------------------
#149  ------K-----------------------------I-----------K----------------------
```

MEANS AND METHODS FOR PRODUCING HIGH AFFINITY ANTIBODIES

CROSS-REFERENCE TO RELATED APPLICATION(S)

This is a national phase entry under 35 U.S.C. §371 of International Patent Application PCT/NL2010/050458, filed Jul. 15, 2010, published in English as International Patent Publication WO 2011/008093 A1 on Jan. 20, 2011, which claims the benefit, under Article 8 of the Patent Cooperation Treaty (PCT), of European Patent 09165603.3, filed Jul. 15, 2009, and both under Article 8 of the PCT and under 35 U.S.C. §119(e) to U.S. Provisional Patent Application Ser. No. 61/225,882 filed Jul. 15, 2009.

FIELD

The invention relates to the field of cell biology. More specifically, the invention relates to the field of antibody production. The invention provides methods and means for the in vitro production and/or selection of highly specific antibodies.

Stable monoclonal cell lines of immortalized human primary B-cells that express the B-cell receptor (BCR) on their cell surface while secreting antibodies are attractive tools for studying various aspects of BCR signaling but also for the generation of human monoclonal antibodies. BCR expression on polyclonal immortalized human B-cells would facilitate selection of antigen—specific cells on basis of binding of antigen to the specific BCR, while production of antibodies enables selection of B-cell clones on the basis of functional activities of the secreted antibodies. While naïve and memory B-cells express cell surface BCR, they do not secrete Ig. It is possible that cells that both express the BCR and secrete antibodies are present in the germinal center (GC) light zone. These cells may represent plasmablasts ready to be selected into the plasma cell compartment.

The GC consists of two areas, the dark and the light zone, which are populated by centroblasts and centrocytes, respectively. Antigen-activated naïve and memory B-cells in the GC undergo extensive proliferation, accompanied by somatic hypermutations (SHM) and class-switch recombination (CSR) of Ig genes, processes both mediated by Activation Induced Cytidine Deaminase (AID). Light zone GC B-cells then undergo selection via BCR—antigen interaction on follicular dendritic cells and receive help from follicular T helper cells, ultimately developing into memory or antibody-secreting plasma cells. These selected light zone GC B-cells express Bcl-xL, a member of the anti apoptotic Bcl-2 protein family most likely to protect them against cell death. Somatic hypermutations and class-switch recombination of Ig genes no longer occur in the light zone.

Mature B-cells can be cultured in vitro under conditions which mimic some key aspects of the GC reaction; that is, activation of B-cells with CD40 ligand (L) and the presence of cytokines like interleukin (IL)-4, IL-10 or IL-21. While B-cells cultured with CD40L, IL-2 and IL-4 produce very little Ig, addition of IL-21 leads to differentiation to plasma cells accompanied by high Ig secretion (Ettinger, R. et al. J Immunol 175, 7867-79 (2005); Kuo, T. C. et al. J Exp Med 204, 819-830 (2007)). Although this in vitro system has proven useful to study some aspects of B-cell differentiation, both naïve IgD+ B-cells and switched IgD− memory B-cells eventually differentiate into terminally differentiated plasma cells, which is accompanied by cell cycle arrest precluding the generation of long-term antigen-specific BCR positive cell lines.

Recent advances have provided insight into how multiple transcription factors, including B-lymphocyte-induced maturation protein 1 (BLIMP1), X-box-binding protein 1 (XBP1) and B-cell lymphoma (BCL)6 control development of GC B-cells into terminally arrested, antibody-producing plasma cells. The transcriptional repressor BCL6 has been shown to prevent plasma cell differentiation. BCL6 is highly expressed in GC B-cells were it facilitates expansion of B-cells by downregulating p53 and prevents premature differentiation of GC cells into plasma cells by negatively regulating BLIMP1.

Ex vivo cell cultures are important tools in current biological and medical applications. One important application is culturing antibody producing cells in order to harvest antibodies, preferably monoclonal antibodies. Monoclonal antibodies (mAbs) represent multiple identical copies of a single antibody molecule which copies bind to antigens with the same affinity and promote the same effector functions. Amongst the benefits of mAbs is their specificity for the same epitope on an antigen. This specificity confers certain clinical advantages on mAbs over more conventional treatments while offering patients an effective, well tolerated therapy option with generally low side effects. Moreover mAbs are useful for biological and medical research.

It is an object of the present invention to provide a method for producing and/or selecting high affinity antibodies.

The invention provides a method for modulating the occurrence of somatic hypermutations in an antibody producing plasmablast-like B-cell, comprising inducing, enhancing and/or maintaining expression of Bcl-6 in a B-cell and inducing, enhancing and/or maintaining expression of an anti-apoptotic nucleic acid in said B-cell, thus generating an antibody producing plasmablast-like B-cell, wherein the method further comprises modulating the functional activity of AID in said B-cell.

Preferably, a memory B-cell with a desired specificity is isolated and subjected to a method according to the present invention, so that antibody producing plasmablast-like B-cells with a desired specificity are obtained. Further provided is thus a method for modulating the occurrence of somatic hypermutations in an antibody producing plasmablast-like B-cell, comprising inducing, enhancing and/or maintaining expression of Bcl-6 in a memory B-cell and inducing, enhancing and/or maintaining expression of an anti-apoptotic nucleic acid in said memory B-cell, thus generating an antibody producing plasmablast-like B-cell; the method further comprising modulating the functional activity of AID in said memory B-cell and/or in said antibody producing plasmablast-like B-cell. Preferably, the functional activity of AID in said memory B-cell is modulated. Said memory B-cell subsequently becomes a plasmablast-like antibody producing cell wherein the functional activity of AID is modulated.

As used herein, the term "anti-apoptotic nucleic acid" refers to a nucleic acid which is capable of delaying and/or preventing apoptosis in a B-cell. Preferably, said anti-apoptotic nucleic acid is capable of delaying and/or preventing apoptosis in a plasmablast-like antibody producing B-cell. Preferably, an anti-apoptotic nucleic acid is used which comprises an exogenous nucleic acid. This means that either a nucleic acid sequence is used which is not naturally expressed in plasmablasts, or that an additional copy of a naturally occurring nucleic acid is used, so that expression in the resulting plasmablast-like B-cells is enhanced as compared to natural plasmablasts. Various anti-apoptotic nucleic acids are known in the art, so that various embodiments are available. Preferably, an anti-apoptotic nucleic acid is used which is an anti-apoptotic member of the Bcl-2 family because anti-apoptotic Bcl-2 proteins are good apoptosis inhibiters. Many processes that are controlled by the Bcl-2 family (which family includes both pro- and anti-apoptotic proteins) relate to the mitochondrial pathway of apoptosis, as outlined in more detail herein below. Anti-apoptotic Bcl-2 family members Bcl-2, Bcl-xL, Bcl-w, A1 and Mcl-1 are generally integrated with the outer mitochondrial membrane. They directly bind and inhibit the pro-apoptotic proteins that belong to the Bcl-2 family to protect mitochondrial membrane integrity.

In a particularly preferred embodiment said anti-apoptotic nucleic acid encodes Bcl-xL and/or Mcl-1 and/or a functional part of Bcl-xL and/or a functional part of Mcl-1. As demonstrated in the examples, a combination of Bcl-6 and Bcl-xL nucleic acids, as well as a combination of Bcl-6 and Mcl-1 nucleic acids, is particularly suitable for immortalizing B-cells and long term culture of the resulting plasmablast-like B-cells. Most preferably, said anti-apoptotic nucleic acid encodes Bcl-xL or a functional part thereof, because a combination of Bcl-6 and Bcl-xL stabilizes B-cells particularly well.

A functional part of Bcl-xL and a functional part of Mcl-1 are defined herein as fragments of Bcl-xL and Mcl-1, respectively, which have retained the same kind of anti-apoptotic characteristics as full length Bcl-xL and Mcl-1, respectively, in kind (but not necessarily in amount). Functional fragments of Bcl-xL and Mcl-1 are typically shorter fragments of Bcl-xL and Mcl-1 which are capable of delaying and/or preventing apoptosis in a B-cell. Such functional fragments are for instance devoid of sequences which do not contribute to the anti-apoptotic activity of Bcl-xL or Mcl-1.

Said antibody producing cell preferably comprises a mammalian cell. Non-limiting examples include antibody producing cells derived from a human individual, rodent, rabbit, llama, pig, cow, goat, horse, ape, chimpanzee, macaque and gorilla. Preferably, said antibody producing cell comprises a human cell, a murine cell, a rabbit cell, an ape cell, a chimpanzee cell, a macaque cell and/or a llama cell. Most preferably, said antibody producing cell comprises a human B-cell.

In a preferred embodiment, said memory B-cell is a human memory B-cell. In yet another preferred embodiment, said memory B-cell is a peripheral blood memory B-cell. Peripheral blood memory B-cells are easily obtained, without much discomfort for the individual from which they are derived, and appear to be very suitable for use in a method according to the present invention.

The present inventors surprisingly found that modulation of the functional activity of AID affects the occurrence of somatic hypermutations in an antibody producing plasmablast-like B-cell. It is well documented that human naive and memory B-cells can be cultured for a limited period following engagement of CD40 in the presence of cytokines, including IL-2, IL-4 and IL-10 (Rousset F et al. PNAS 89, 1890-1893 (1992); Banchereau J et al. Science 251, 70-72 (1991)) and it is believed that this system mimics the in vivo response of B-cells towards cognate antigen primed CD40L-expressing helper T cells. The mechanisms of regulation of survival and proliferation of mature B-cells cultured under these conditions are, however, only partly known.

An antibody producing plasmablast-like B-cell is defined as a cell which is capable of proliferating and capable of producing and/or secreting antibody or a functional equivalent thereof. Said antibody producing plasmablast-like B-cell is stable for at least six weeks, more preferably at least nine weeks, more preferably for at least three months, more preferably for at least six months.

An improved method for generating an antibody-producing plasmablast-like B-cell was recently described in PCT/NL2008/050333, which is hereby incorporated by reference. According to this method, the amount of Bcl-6 and a Bcl-2 family member, preferably Bcl-xL, are modulated in a B-cell, preferably a memory B-cell, to generate an antibody-producing plasmablast-like B-cell. In PCT/NL2008/050333 the amount of Bcl-6 and/or Bcl-xL expression product is either directly or indirectly influenced. Preferably the amounts of both Bcl-6 and Bcl-xL expression products within said antibody producing cell are increased, since both expression products are involved in the stability of an antibody producing memory B-cell. Said Bcl-xL is a member of the anti-apoptotic Bcl-2 family. Processes that are controlled by the Bcl-2 family, which includes both pro- and anti-apoptotic proteins, relate to the mitochondrial pathway of apoptosis. This pathway proceeds when molecules sequestered between the outer and inner mitochondrial membranes are released into the cytosol by mitochondrial outer membrane permeabilization. The pro-apoptotic family members can be divided in two classes. The effector molecules Bax and Bak, which contain so-called Bcl-2 homology domain 3 (BH3) domains, are involved in permeablilizing the outer mitochondrial membrane by forming proteolipid pores; the pro-apoptotic BH3-only proteins (Bad, Bik, Bim, Bid, Hrk, Bmf, bNIP3, Puma and Noxa) function upon different cellular stresses by protein-protein interactions with other (anti-apoptotic) Bcl-2 family members (Boise, L. H. et al. Cell 74, 597-608 (1993); Adams J. M. et al. Current Opinion in Immunology 19, 488-496 (2007); Chipuk, J. E. et al. Trends in Cell Biol 18, 157-163 (2007)). Anti-apoptotic Bcl-2 family members Bcl-2, Bcl-xL, Bcl-w, A1 and Mcl-1 are generally integrated with the outer mitochondrial membrane. They directly bind and inhibit the pro-apoptotic Bcl-2 proteins to protect mitochondrial membrane integrity.

It is furthermore preferred that said antibody producing plasmablast-like B-cell is incubated with IL 21 and CD40L. A B-cell, such as an antibody producing plasmablast-like B-cell, is preferably cultured in the presence of CD40L since replication of most B-cells is favored by CD40L. It is furthermore preferred that STAT3 is activated in said antibody producing memory B-cell. Activation of STAT3 can be achieved in a variety of ways. Preferably, STAT3 is activated by providing an antibody producing cell with a cytokine. Cytokines, being naturally involved in B-cell differentiation, are very effective in regulating STAT proteins. Very effective activators of STAT3 are IL 2, IL 10, IL 21 and IL 6, but also IL 7, IL 9, IL 15, IL 23 and IL 27 are known to activate STAT3. Additionally, or alternatively, STAT3 activation is accomplished by transfer into a B-cell of a nucleic acid encoding a mutant of STAT3 that confers constitutive activation to STAT3. (Sean A Diehl, Heike Schmidlin, Maho Nagasawa, Simon D van Haren, Mark J Kwakkenbos, Etsuko Yasuda, Tim Beaumont, Ferenc A Scheeren, Hergen Spits STAT3-mediated up-regulation of BLIMP1 is coordinated with BCL6 down-regulation to control human plasma cell differentiation J Immunol 2008 vol. 180 (7) pp. 4805-15)

Most preferably IL 21 is used, since IL 21 is particularly suitable for influencing the stability of an antibody producing plasmablast-like B-cell. In addition to upregulating STAT3, IL 21 is capable of upregulating Blimp 1 expression even when Blimp 1 expression is counteracted by BCL6. With the methods disclosed in PCT/NL2008/050333, it has become possible to increase the replicative life span of an antibody producing cell since it is possible to maintain a B-cell in a developmental stage wherein replication occurs. In earlier ex vivo B-cell cultures the replicative life span was only a few weeks to two months. During this time the cultured cells lose their capability of replicating, their capability of producing antibody and/or their capability of developing into a cell that produces antibodies. With a method as disclosed in PCT/NL2008/050333, however, it has become possible to prolong the replicative life span of antibody producing memory B-cells, so that ex vivo cultures are generated comprising plasmablast-like B-cells that are capable of replicating and producing antibody.

Activation-induced cytidine deaminase (AID) deaminates deoxycytidine residues in immunoglobulin genes, which triggers antibody diversification. It was demonstrated in patent application US2008305076 that IL 21 induces BLIMP, Bcl-6 and AID expression, but not somatic hypermutation. In contrast to this demonstration, the present inventors were able to show that modulation of the functional activity of AID in an antibody producing plasmablast-like B-cell that is stimulated with IL 21 clearly results in modulation of the incidence of somatic hypermutations. Hence, contrary to the teaching of US2008305076, the present invention provides methods wherein B-cells are cultured in the presence of IL 21 and CD40L and wherein the occurrence of somatic hypermutations in antibody-producing plasmablast-like B-cells is modulated.

In one embodiment, the functional activity of AID is reduced in an antibody producing plasmablast-like B-cell. This results in a reduction of the occurrence of somatic hypermutations in said antibody producing plasmablast-like B-cell. The functional activity of AID is preferably reduced by reducing the expression and/or specific activity of AID in the antibody producing plasmablast-like B-cell. As explained above, in a preferred embodiment the functional activity of AID is reduced in a B-cell (such as a memory B-cell) which subsequently develops into a plasmablast-like B-cell. This allows a relatively simple procedure wherein a B-cell with a specificity of interest is harvested, where after the functional activity of AID in said cell is reduced and expression of Bcl-6 and of an anti-apoptotic nucleic acid in said cell are induced, enhanced or maintained. Said cell subsequently develops into an antibody producing plasmablast-like B-cell wherein the functional activity of AID is reduced, so that the occurrence of somatic hypermutations in the resulting antibody producing plasmablast-like B-cells during prolonged culturing is reduced. It is also possible to provide a memory B-cell with a nucleic acid sequence which is capable of conditionally reducing AID activity. In this embodiment, AID activity in a memory B-cell or in the resulting plasmablast-like B-cells is regulated at will.

Methods for reducing the expression of AID are known in the art. A reduction of the level of expression of AID can be achieved at the transcriptional level, the mRNA level, or the protein level, or a combination thereof. Said reduction preferably is to a level of at most 75%, more preferred at most 60%, more preferred at most 50%, more preferred at most 40%, more preferred at most 30%, more preferred at most 20%, more preferred at most 10%, more preferred at most 5% or the level of expression at which AID is expressed in a non-treated antibody producing plasmablast-like B-cell.

A reduction of the level of expression of AID is, for example, achieved by introduction into a B-cell (preferably a memory B-cell) of a (non-natural) zinc-finger protein that has been modified to be able to bind to the promoter region of AID and which is coupled to a transcriptional repressor domain, such as a Kruppel-associated box A/B repressor domain.

Methods for designing Zinc-finger proteins that bind specific nucleotide sequences are known in the art and are disclosed, for example by Tan S et al. PNAS 100, 11997-12002 (2003), which is herewith enclosed by reference.

As a further example, a reduction of the level of expression of AID can be achieved by introduction of a molecule into a B-cell that interferes with the transcriptional activation of AID in an antibody producing plasmablast-like B-cell. It is known that the expression of AID is modulated by basis Helix-Loop-Helix (bHLH) proteins such as, for example, E47 and E12, which are both encoded by the E2A gene. bHLH transcription factors are known to form homodimers and/or heterodimers. A molecule that interferes with the homo- or heterodimerization of E47 and/or E12 thus will interfere with the transcriptional activation of AID in the antibody producing plasmablast-like B-cell. Therefore, introduction into a B-cell of a molecule that interferes with the homo- or heterodimerization of E47 and/or E12 results in a reduction of the level of expression of AID.

In one embodiment, said molecule is a compound molecule. The term "compound" refers to inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates. Libraries of compounds, such as peptide libraries (e. g. LOPAP™, Sigma Aldrich), lipid libraries (BioMol), synthetic compound libraries (e. g. LOPAC™, Sigma Aldrich) or natural compound libraries (Specs, TimTec), can be screened for identifying one or more compounds that bind and interfere with the homo- or heterodimerization of E47 and/or E12, and thus with the transcriptional activation of E47 and/or E12 homo- or heterodimers.

The binding affinity of a compound to a E47 and/or E12 polypeptide is measured by any method known in the art, such as for instance using surface plasmon resonance biosensors (Biacore), by saturation binding analysis with a labeled compound (e. g. Scatchard and Lindmo analysis), by differential UV spectrophotometer, fluorescence polarisation assay, Fluorometric Imaging Plate Reader (FLIP@) system, Fluorescence resonance energy transfer, or Bioluminescence resonance energy transfer. The binding affinity of compounds can also be expressed in a dissociation constant (Kd) or as IC50 or EC50. The IC50 represents the concentration of a compound that is required for 50% inhibition of binding of a dimerization partner to the polypetide. The EC50 represents the concentration required for obtaining 50% of the maximum effect in any assay that measures dimerization and/or transcriptional activation of E47 and/or E12 homo- or heterodimers. The dissociation constant, Kd, is a measure of how well a compound binds to the polypeptide, it is equivalent to the compound concentration required to saturate exactly half of the binding-sites on the polypeptide. Compounds with a high affinity binding have low Kd, IC50 and EC50 values, i.e. in the range of 100 nM to 1 pM; a moderate to low affinity binding relates to a high Kd, IC50 and EC50 values, i.e. in the micromolar range.

Preferably the compounds are low molecular weight compounds. Low molecular weight compounds, i.e. with a molecular weight of 500 Dalton or less, have good absorption and permeation in biological systems and are consequently more likely to be successful drug candidates than compounds with a molecular weight above 500 Dalton.

In a preferred method according to the invention, said molecule is an inhibitor of DNA binding (ID). The ID proteins comprise a family of four which are called ID1, ID2, ID3 and ID4 and which are capable of dimerizing with E12 and/or E47 bHLH proteins and prevent the DNA binding of these bHLH proteins. Expression of AID is preferably modulated by (over)expression of ID proteins in said antibody producing plasmablast-like B-cell. Most preferred molecules are ID2 and, even more preferred, ID3. ID proteins have been described to be involved in regulation of AID expression via binding to, and regulation of the E-proteins, especially E47 (Kee B. L. Nat Rev Immunol 9, 175-84 (2009)). It was found by the present inventors that AID expression levels in antibody producing plasmablast-like B-cells decline in the presence of ID proteins. Cell growth is a little hampered in cells expressing ID2, in addition to Bcl-6 and Bcl-xL. This is not the case for ID3. The use of ID3 is therefore preferred. Thus, by overexpression of ID, the expression of AID and subsequent accumulation of somatic mutations in VH and VJ chains of the immunoglobulins that are expressed in the antibody producing plasmablast-like B-cell, are limited or even blocked. Preferably, ID is conditionally expressed in said antibody producing plasmablast-like B-cell, for instance after administration of a certain inducer. This way, the extent of ID expression—and, hence, the extent of AID expression—is regulated at will. Non-limiting examples of conditional expression systems are described herein below.

In yet a further preferred embodiment, said molecule is an antisense nucleic acid and/or ribozyme, preferably a full length hammerhead ribozyme, directed against E12 and/or E47. Said antisense nucleic acid preferably comprises a stretch of more than 50 nucleic acid molecules that are antisense to and can base pair with an RNA transcript encoding the E12 and/or E47 protein. Expression of antisense RNA often leads to the formation of double stranded RNA molecules, comprising the antisense RNA and the endogenous sense mRNA. This double stranded RNA molecule prevents the mRNA from being translated into protein.

In yet a further preferred embodiment, said molecule is a dsRNA molecule that induces mRNA degradation employing RNA interference (RNAi). RNAi is based on the generation of short, double-stranded RNA (dsRNA) which activates a normal cellular process leading to a highly specific RNA degradation (Zamore et al. Cell 101, 25-33 (2000)) and/or suppression of translation. Recent studies have demonstrated that RNA interference is mediated by the generation of 18- to 23-nucleotide dsRNA molecules with 2 nucleotide-long 3' overhangs termed small interfering RNA (siRNA) duplexes. RNAi allows silencing of a gene on the basis of its sequence. For expression of dsRNA molecules in an antibody producing plasmablast-like B-cell, an expression cassette encoding the two strands of the dsRNA duplex molecule preferably comprise a polymerase III enhancer/promoter. A preferred polymerase III enhancer/promoter is selected from the U6 and H1 promoter. A polymerase III enhancer/promoter preferably drives expression of small interfering RNA (siRNA) strands that upon duplex formation by base-pairing comprise 18-23 (typically 19) nucleotide-long double-stranded siRNA molecules with 2 nucleotide-long 3' overhangs with one of the strands exhibiting extensive homology to a part of a mRNA transcript encoding the E12 and/or E47 bHLH protein. Said siRNA activates the RNA interference (RNAi) pathway and interferes with the expression of said gene.

An expression cassette for expression of an antisense RNA acid and/or a ribozyme or of a protein, such as a zinc-finger protein or an ID protein, preferably comprises an enhancer/promoter that is suitable for expressing an RNA molecule in said cell line, and a transcription stop signal, such as, for example a poly(A) signal if the promoter is a polymerase II promoter. Said enhancer/promoter and transcription stop signal are preferably functionally linked to drive expression of the RNA in the cell line. Said enhancer/promoter is preferably either a polymerase II promoter or a polymerase III enhancer/promoter. A polymerase II enhancer/promoter drives expression of predominantly precursors of mRNA. A preferred polymerase II enhancer/promoter is selected from the immediate early gene of human cytomegalovirus, the SV40 promoter, and the long terminal repeat of Rous sarcoma virus.

In a preferred embodiment of the invention the functional activity of AID in an antibody producing plasmablast-like B-cell is modulated by conditional expression of, for example, a zinc finger protein or of ID, preferably ID2 and/or ID3. Said B-cell is also transduced with Bcl-6 and an anti-apoptotic nucleic acid. Increased gene expression of, for example, ID2 and/or ID3 can be obtained by making gene expression dependent on the presence of an inducer. In addition, a reduction of the level of AID expression can be obtained by RNA interference in which expression of the dsRNA molecule is dependent on the presence of an inducer. Several inducible gene expression systems are currently available that can be used to control expression of AID, ID2 and/or ID3, dsRNA, an antisense RNA, a ribozyme, and/or a Zinc finger protein.

Tet-On and Tet-Off expression systems (for example Tet-On® and Tet-Off® Advanced Inducible Gene Expression Systems, Clontech) can be used for inducible expression of a gene of interest. In these systems expression of the transcriptional activator (tTA) is regulated by the presence (Tet-On) or absence (Tet-Off) of tetracycline (TC) or a derivative like doxycycline (dox). In principle, tTA is composed of the Escherichia coli Tet repressor protein (TetR) and *Herpes simplex* virus transactivating domain VP16. tTA regulates transcription of a gene of interest under the control of a tetracycline-responsive element (TRE) comprising the Tet operator (TetO) DNA sequence and a promoter sequence, for instance the human cytomegalovirus (hCMV) promoter (Baron, U. and Bujard, H. Methods Enzymol 327, 401-21 (2000)). A gene encoding, for example, ID2 and/or ID3 and/or a zinc finger protein can be placed downstream of this promoter. Preferably, for the expression of dsRNA a RNA polymerase III promoter is used such as H1 and U6.

In the Tet-off system, tTA binds to TRE in the absence of TC or dox (Gossen, M. and Bujard, H. PNAS 89, 5547-51 (1992)) and transcription of, for example, ID2 and/or ID3 gene, dsRNA and/or a gene encoding a zinc finger protein is activated, whereas in the presence of TC or dox tTA cannot bind TRE and expression of, for example, ID2 and/or ID3 gene, dsRNA and/or a gene encoding a Zinc finger protein is inhibited. In contrast, the Tet-on system uses a reverse tTA (rtTA) that can only bind the TRE in the presence of dox (Gossen, M. et al. Science 268, 1766-9 (1995)). Transcription of, for example, ID2 and/or ID3 gene, dsRNA and/or a gene encoding a zinc finger protein is inhibited in the absence of dox and activated in the presence of dox.

In another embodiment, inducible expression is executed using a hormone inducible gene expression system such as for instance an ecdysone inducible gene expression system (for example RheoSwitch®, New England Biolabs) (Christopherson, K. S. et al. PNAS 89, 6314-8 (1992)). Ecdysone is an insect steroid hormone from for example *Drosophila melanogaster*. In cells transfected with the ecdysone receptor, a heterodimer consisting of the ecdysone receptor (Ecr) and retinoid X receptor (RXR) is formed in the presence of an ecdyson agonist selected from ecdysone, one of its analogues such as muristerone A and ponasterone A, and a non-steroid ecdysone agonist. In the presence of an agonist, Ecr and RXR interact and bind to an ecdysone response element that is present on an expression cassette. Transcription of a protein that is placed in an expression cassette downstream of the ecdysone response element is thus induced by exposing the antibody producing plasmablast-like B-cell to an ecdyson agonist.

In yet another embodiment of the invention inducible expression is executed using an arabinose-inducible gene expression system (for example pBAD/gIII kit, Invitrogen) (Guzman, L. M. et al. Bacteriol 177, 4121-4130 (1995)). Arabinose is a monosaccharide containing five carbon atoms. In cells transfected with the arabinose-inducible promoter PBAD transcription of a gene placed downstream of PBAD can be then induced in the presence of arabinose.

In yet a further embodiment, the functional activity of AID is reduced by reducing the specific activity of AID in the antibody producing plasmablast-like B-cell. A reduction of the specific activity of AID is for instance achieved by addition of a compound that interferes with the enzymatic activity of AID. A preferred compound is a low molecular weight compound. Low molecular weight compounds, i.e. with a molecular weight of 500 Dalton or less, have good absorption and permeation in biological systems and are consequently more likely to be successful drug candidates than compounds with a molecular weight above 500 Dalton. Libraries of compounds, such as peptide libraries (e. g. LOPAP™, Sigma Aldrich), lipid libraries (BioMol), synthetic compound libraries (e. g. LOPAC™, Sigma Aldrich) or natural compound libraries (Specs, TimTec), are available that can be screened for identifying one or more compounds that binds and interferes with the activity of AID. Methods for determining the activity of AID are known in the art. For example, cytidine deaminase activity can be measured in a bacterial mutator assay, in which AID-mediated DNA deamination at cytidine residues results in increased frequency of rifampicin (Rif)-resistant bacterial colonies bearing mutations at the gene coding for the Rif target, RNA. Alternatively, or in addition, complementation tests can be performed in AID-deficient mouse B-cells, for instance as described in Ichikawa et al. J. Immunol. 177, 355-361 (2006).

In yet another embodiment, the amount of AID in an antibody producing plasmablast-like B-cell is increased, preferably by administration of an AID-encoding nucleic acid sequence to a B-cell, preferably a memory B-cell. It is sometimes preferable to temporarily increase the amount of AID in order to increase somatic hypermutations in the B-cells, thereby obtaining improved variants of an original antibody of interest. Such improved variant is preferably an antibody with an increased affinity and/or specificity, as compared to said original antibody of interest. When a plasmablast-like B-cell has been obtained which produces a variant of interest, the functional activity of AID is preferably subsequently reduced in order to counteract further somatic hypermutations in said B-cell.

In a further embodiment, the invention provides an antibody producing plasmablast-like B-cell obtainable by a method according to the invention. In preferred embodiments, plasmablast-like B-cells are produced wherein AID expression is reduced by expression of ID proteins. Further provided is therefore an isolated or recombinant antibody producing B-cell which expresses Bcl-6 and an anti-apoptotic nucleic acid and an ID protein. In one preferred embodiment, ID2 and/or ID3 are expressed. Further provided is therefore an isolated or recombinant antibody producing B-cell which expresses Bcl-6 and an anti-apoptotic nucleic acid and an ID protein selected from the group consisting of ID2 and ID3. Said anti-apoptotic nucleic acids preferably comprise an exogenous nucleic acid, as described herein before. In one preferred embodiment, an anti-apoptotic nucleic acid is used which is a member of the Bcl-2 family. Preferably, said anti-apoptotic nucleic acid comprises Bcl-xL or Mcl-1 or a functional part of Bcl-xL or a functional part of Mcl-1. Further provided is therefore an isolated or recombinant antibody producing B-cell which expresses Bcl-6 and an ID protein and a nucleic acid sequence encoding a compound selected from the group consisting of Bcl-xL and Mcl-1 and a functional part of Bcl-xL and a functional part of Mcl-1.

Preferably, said antibody producing B-cell comprises exogenous nucleic acids. Further provided is therefore an isolated or recombinant antibody producing B-cell which comprises an exogenous nucleic acid encoding Bcl-6 and an exogenous nucleic acid encoding an ID protein and an exogenous nucleic acid encoding a compound selected from the group consisting of Bcl-xL and Mcl-1 and a functional part of Bcl-xL and a functional part of Mcl-1. As said before, said ID protein preferably comprises ID2 and/or ID3. One preferred embodiment therefore provides an isolated or recombinant antibody producing B-cell which comprises an exogenous nucleic acid encoding Bcl-6 and an exogenous nucleic acid encoding ID2 and an exogenous nucleic acid encoding a compound selected from the group consisting of Bcl-xL and Mcl-1 and a functional part of Bcl-xL and a functional part of Mcl-1. Yet another preferred embodiment provides an isolated or recombinant antibody producing B-cell which comprises an exogenous nucleic acid encoding Bcl-6 and an exogenous nucleic acid encoding ID3 and an exogenous nucleic acid encoding a compound selected from the group consisting of Bcl-xL and Mcl-1 and a functional part of Bcl-xL and a functional part of Mcl-1.

An isolated or recombinant antibody producing plasmablast-like B-cell which is obtained by any method according to the present invention is also provided.

As outlined above, increasing AID in (a B-cell which will develop into) an antibody producing plasmablast-like B-cell allows the generation of novel immunoglobulins that harbor mutations that were not present in the B-cell before transduction with BCL6 and an anti-apoptotic nucleic acid. For example, culturing plasmablast-like B-cells in which somatic hyper mutation is induced by expression of AID will allow to obtain one or more immunoglobulin variants which, for example, have a higher affinity for a ligand that is recognized by the immunoglobulin, or that are more stable, for example, in an aqueous solution or under increased salt conditions, or any combination thereof. In yet another embodiment an immunoglobulin variant is selected with reduced or lost binding to the original antigen. By analyzing the VH and VL sequences, it is possible to determine the immunoglobulin residues important for antigen binding. Therefore, the invention further provides a use of a B-cell with increased expression and/or activity of AID for increasing the occurrence of somatic hypermutations in an antibody producing memory B-cell.

In a further embodiment, the invention provides a use of an antibody producing plasmablast-like B-cell with reduced expression and/or activity of AID and thus a reduced occurrence of somatic hypermutations for large scale production of antibodies. Culturing plasmablast-like B-cells in which somatic hyper mutation is reduced or even inhibited by reduction of the functional activity of AID will allow these cells to produce immunoglobulins with a lower risk of obtaining unwanted variants. With the term large scale production is meant the production of antibodies by the antibody producing plasmablast-like B-cell beyond the exploratory level, i.e. not for identifying an immunoglobulin. Said large scale production preferably refers to a culture comprising at least 1 milliliter of culture medium, more preferred at least 5 milliliter, more preferred at least 10 milliliter, more preferred at least 25 milliliter, more preferred at least 50 milliliter, more preferred at least 100 milliliter, more preferred at least 1000 milliliter.

The invention further provides an antibody that is produced by an antibody producing plasmablast-like B-cell according to the present invention. Said antibody preferably is a human antibody.

The invention is further explained by the following, non-limiting examples.

FIGURE LEGENDS

FIG. 1

CD27+ memory peripheral blood cells acquire a stable GC-like phenotype following transduction with BCL6 and Bcl-xL and subsequent culture (throughout the patent application these cells are named "antibody producing plasmablast-like cells"). (a) Phenotype of BCL6+Bcl-xL transduced CD27+ memory B-cells (6XL, black histogram line) compared to tonsil GC cells (GC, CD38$^+$CD20$^+$, shaded grey), tonsil naïve and memory cells (N/M, CD38$^-$ CD20$^{low}$, light gray histogram line), and tonsil plasma cells (PC, CD38$^{++}$CD20$^{low}$, dark gray histogram line). BCL6+Bcl-xL transduced monoclonal cell lines show an identical phenotype (not shown). (b) Relative mRNA levels of AICDA (encoding AID) in CD19$^+$IgG$^+$CD27$^+$ PB memory B-cells and CD19$^+$CD38$^+$CD20$^+$IgD$^-$ tonsillar GC B-cells (value set as 1) compared to BCL6+Bcl-xL transduced bulk CD27$^+$ memory cells using quantitative RT-PCR.

FIG. 2

Expression and activity of AID in BCL6+Bcl-xL transduced cells. (a) Overview of all D25 subclones that had one or more amino acid substitutions, additional silent mutations are shown in italic. (b) mRNA levels of AICDA (encoding AID) in CD19$^+$CD38$^+$CD20$^+$IgD$^-$ tonsillar GC B-cells and CD19$^{30}$ IgG$^+$CD27$^+$ PB memory B-cells compared to 23 BCL6+Bcl-xL transduced monoclonal cell lines and monoclonal anti-RSV specific cell line D25, using quantitative RT-PCR. (c) Percentage of subclones with indicated number of VH mutations, as percentage of total number of subclones sequenced. (d) Location of VH mutations, percentage of mutations per VH region per basepair. (e) Binding of D25-subclone Ig to RSV infected HEp2 cells. Squares are individual D25 subclones, black circles rD25. Grey circles indicate clones with deviating affinity.

FIG. 3

Id regulates AID expression in BCL6 Bcl-xL transduced B-cells (a) mRNA levels of AICDA in the monoclonal anti-RSV specific cell line D25 transduced with Control-YFP, AID-YFP, ID2-YFP or ID3-YFP using quantitative RT-PCR. (b) Growth curves of the monoclonal anti-RSV specific cell line D25 transduced with Control-YFP, AID-YFP, ID2-YFP or ID3-YFP.

FIG. 4

Enhanced binding and competition of B-cell supernatant derived and recombinant protein of mutated D25 clones to RSV infected HEp2 cells. (a) titration of B-cell culture supernatant of 2 clones that were selected based on two identical amino acid substitutions and one additional mutation compared to the original D25 sequence (#29: S83Y/V111I/V112L and #189: G63D/V111I/V112L), one clone that lost binding to RSV infected cell (#77; E107K) and an unmutated D25 clone (#54). The mutated clones were selected retrospectively after 1) two tests in which both culture IgG levels were determined and binding to RSV infected HEp2 was performed. The Igs that showed enhanced binding were ranked in a top 25. When an Ig was in the top 25 twice it was selected and 2) then tested in a competition experiment were they had to compete out the original D25 clone and 3) had mutations that could explain the phenotype seen in the above-mentioned experiments. Replacement was performed as follows: saturate RSV infected Hep2 cells with PE labeled D25, wash 3× and incubate with 250 ng ml$^{-1}$ D25-PE+ rising amount of competing D25 subclone (0-800 ng ml$^{-1}$) incubate for 3 hrs at 37° C., wash 2× and analyze on FACS (b) D25 competition by same clones. Incubate RSV infected Hep2 cells with 250 ng ml$^{-1}$ D25-PE+ rising amount of competing D25 subclone (0-800 ng ml$^{-1}$) (same mix as was used for replacement assay), incubate for 30 minutes at 4° C., wash 2× and analyze on FACS.

FIG. 5

Transduction of human IgG+ memory B cells with BCL6, Bcl-xL and MCL-1. Shown are FACS analysis of the percentage of GFP (BCL6 or BCL6 and Bcl-xL) and NGFR (Bcl-xL or MCL-1) expressing cells 4 days and 21 days after transduction.

FIG. 6

Expression of MCL1 in combination with BCL6 and/or Bcl-xl results in outgrowth of human memory B cells. Activated CD19$^+$CD27$^+$IgM$^-$IgA$^-$ memory cells were transduced with: (a) BCL6-GFP and MCL-1-NGFR, (b) BCL6-GFP and Bcl-xL-NGFR or (c) BCL6-Bcl-xL-GFP and MCL-1-NGFR and transduction markers were followed in time by FACS analysis. Depicted are the percentage of transduced cells in a bulk culture that were maintained under standard culture conditions, e.g. with irradiated CD40L-L cells and rmIL-21. Cells transduced with BCL6in combination with MCL-1 or Bcl-xL showed growth advantage compared to cells lacking one of these transgenes and ultimately dominated the cultures (>90%).

FIG. 7

Figure 6A:
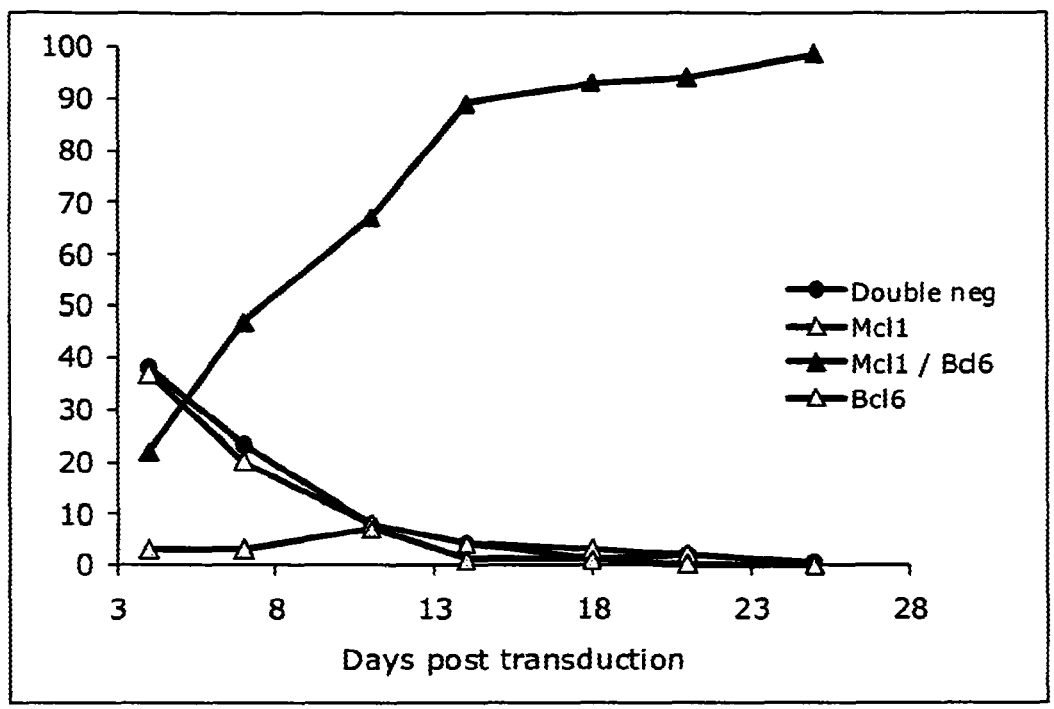
Figure 6B:
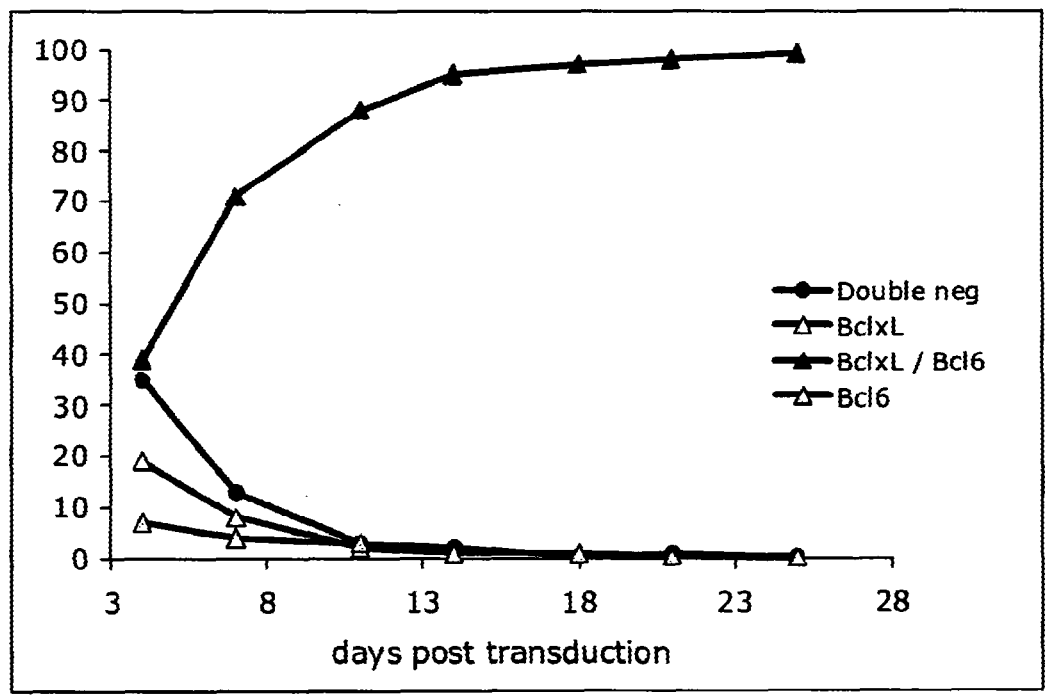
Figure 6C:
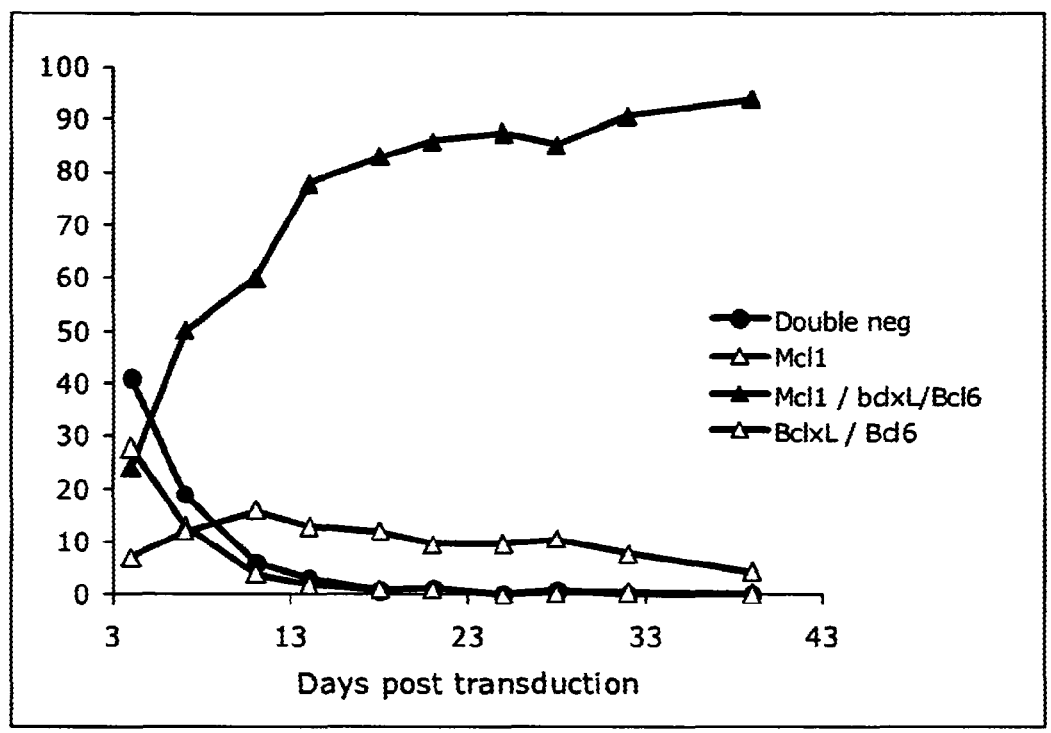

Relative increase in cell numbers of human memory B cells expressing MCL1 in combination with BCL6 and/or Bcl-xl. As in FIG. 6 activated CD19$^+$CD27$^+$IgM$^-$IgA$^-$ memory cells were transduced with: (a) BCL6-GFP and MCL-1-NGFR, (b) BCL6-GFP and Bcl-xL-NGFR or (c) BCL6-Bcl-xL-GFP and MCL-1-NGFR and cell numbers were followed in time by counting. Relative cell numbers were determined by correction for the percentage of cells carrying the transgenes of interest as shown in FIG. 6. Cells expressing BCL6 and MCL-1 did grow out and showed enhanced proliferation compared to cells with BCL6 alone. However, survival and proliferation was most profound for the combination of BCL6 and Bcl-xL alone or in combination with MCL-1. Interestingly, in (c) the BCL6 and Bcl-xL cells did not outgrow cells also containing MCL-1 indicating that addition of MCL-1 is an advantage.

FIG. 8

Relative expansion of number of double transduced cells. Cultures of BCL6, Bcl-xL and MCL1 co-transduced cells were taken 21 days post transduction and were started with equal cell numbers and were set to 1. BCL6/Bcl-xL and BCL6/MCL-1 culture are 100% double transduced at day 21. BCL6/Bcl-xL and MCL-1 was 86% double transduced at day 21 and approximately 96% at day 43. Expansion of BCL6/Bcl-xL and MCL-1 transduced cells is equal to the expansion of BCL6 Bcl-xL transduced cells. Numbers of cells expand at least till day 43 post transduction.

FIG. 9

The phenotype of BCL6, Bcl-xL and MCL-1 transduced cells based on CD20 and CD38 expression on day 4 and 21 after transduction. (a) Cells expressing BCL6 in combination with MCL-1 and/or Bcl-xL acquire a Germinal center-cell like phenotype and are (b) cell surface IgG (BCR) positive, similar to BCL6 Bcl-xL co-transduced cells. Cells lacking BCL6 differentiate toward plasmablast like cells with high CD38 and reduced CD20 expression.

EXAMPLES

Methods

B-cell isolation. We obtained B-cells from peripheral blood (buffy coats from Sanquin) by Ficoll separation and CD22 MACS microbeads (Miltenyi Biotech). Subsequently we sorted these cells for CD19$^+$CD3$^-$CD27$^+$IgM$^-$IgA$^-$ (IgG memory cells) or CD19$^+$CD3$^-$CD27$^+$IgG$^-$IgA$^-$ (IgM memory cells) on a FACSAria (Becton Dickinson).

Tonsil B-cell sorting. We obtained Tonsil B-cells from routine tonsillectomies performed at the Department of Otolaryngology at the Academic Medical Center, Amsterdam, The Netherlands. We separated B-cells by Ficoll and sorted the CD19+CD3−CD44−IgD− GC population. The use of these tissues was approved by the medical ethical committees of the institution.

Cell culture. We maintained B-cells ($2\times10^5$ cells ml$^{-1}$) in IMDM (Gibco) culture medium containing 8% FBS (Gibco), penicillin/streptomycin (Roche) supplemented with recombinant mouse IL 21 (25 ng ml$^{-1}$, R&D systems) and co-cultured them on γ-irradiated (50Gy) mouse L cell fibroblasts stably expressing CD40L (CD40L-L cells, $10^5$ cells ml$^{-1}$). We tested cells routinely by PCR for the presence of mycoplasma and EBV.

Retroviral transduction. The BCL6, ID2 and ID3 retroviral constructs were described previously (Shvarts, A. et al. Genes Dev 16, 681-6 (2002); Jaleco, A. C. et al. Blood 94, 2637-46 (1999); Spits H. et al. J Exp Med 192, 1775-83 (2000)). In brief, we have constructed bicistronic vectors with a gene of interest linked to a downstream internal ribosomal entry site (IRES) and a marker gene that allow independent translation of the products of both genes in the transduced target cells. The ID3 coding sequence was cloned from the pCDNA-Id3 plasmid (gift of Dr C. Murre, University of California at San Diego, San Diego, Calif.). The product was ligated between the Xho I and SnaBI site of the polylinker from our plasmid LZRS-linker-IRES-GFP and/or YFP to obtain the retroviral vector LZRS-Id3-IRES-GFP.

The coding sequence of human ID2 was cut from the pSG5-Id2 vector (a gift of Dr. R. de Groot, University of Utrecht, Utrecht, Netherlands) with Not1 and was ligated in the Not1 site of polylinker from our plasmid LZRS-linker-IRES-GFP and/or YFP. A codon optimized sequence of the phosphorylation-site mutant (S159A) of human MCL-1 (Maurer, U. et al. Mol Cell 21, 749-760 (2006)) was ordered from GeneArt (Regensburg Germany) and cloned into the LZRS retroviral vector. Human Bcl-xL cDNA was cloned into the LZRS retroviral vector and helper-free recombinant retroviruses were produced after transfection into a 293T-based amphotropic retroviral packaging cell line, Phoenix (Kinsella, T. M. et al Hum Gene Ther 7, 1405-1413 (1996)). Human memory B-cells were co-transduced by the different retroviruses after activation on CD40L-L cells in the presence of rmIL-21 for 36 hrs as before (Diehl, S. A. et al. J Immunol 180, 4805-15 (2008)), but in addition cells and virus were centrifuged at room temperature for 60 min at 360×g (1800 RPM).

Flow cytometry. We analyzed stained cells on an LSRII (BD) and processed flow cytometry data with FlowJo software (Tree Star). We purchased the following mAbs against the human molecules from BD-Pharmingen unless otherwise indicated CD3 (SK7), CD10 (HI10a), CD19 (SJ25C1), CD20 (B9E9; Beckman Coulter), CD21 (B-ly4), CD22 (B-ly8; IQ Products), CD25 (BC96; eBioscience), CD27 (O323; eBioscience), CD30 (BerH8), CD38 (HB7), CD40 (MAB89; Beckman Coulter), CD70 (Ki24), CD71 (YDJ1.2.2; Beckman Coulter), CD80 (L307.4), CD86 (2331), CD95 (DX2), CD132 (TUGh4), CD184 (CXCR4, 12G5), CD271 (LNGFR; ME20.4-1.H4; Miltenyi Biotech), CD275 (MIH12; eBioscience), HLA-DR (L243), IgA (F(ab)2; DAKO), IgD (IA6-2), IgG (G18-145), IgM (G20-127) (BD), IL-21R (152512; R&D systems), Ig-kappa (F(ab)2; DAKO, G20-193), and Ig-lambda (F(ab)2; JDC12, DAKO).

RT-PCR. We carried out quantitative RT-PCR with a Bio-Rad iCycler and used the $2^{-(\Delta\Delta C_T)}$ method to calculate relative mRNA expression levels normalized to ACTIN. Primers for AICDA (encoding AID) are described (Smit, L. A. et al. Cancer Res 63, 3894-8 (2003))

ELISA. We coated plates with anti-human IgG Fc-fragment (Jackson ImmunoResearch Laboratories) at 5 µg ml$^{-1}$ in PBS for 1 h at 37° C. or o/n at 4° C. and washed them in ELISA wash buffer (PBS, 0.5% Tween-20). 4% milk in PBS was used as blocking agent, before we added serial dilutions of cell culture supernatants and HRP-conjugated detection Abs (dilutions 1:2500 for HRP-conjugated IgG antibody (Jackson). We used TMB substrate solution (Biosource) for development of the ELISAs.

Cloning and sequencing of mutants of D25. We isolated total RNA using the RNeasy® mini kit (Qiagen), generated cDNA and performed the VH1-69 PCR to determine the sequence of the D25 subclones. From interesting clones (#29, #59, #77, #189) the heavy chain variable region was cloned into the pCR2.1 TA cloning vector (Invitrogen). To rule out reverse transcriptase or DNA polymerase induced mutations, we performed several independent cloning experiments. To produce recombinant D25 mAb we cloned D25 mutated heavy and original light variable regions in frame with human IgG1 and Kappa constant regions into a pcDNA3.1 (Invitrogen) based vector and transiently transfected 293T cells. VL sequences of D25 subclones were also determined but did not harbor any mutations compared to the original D25 light chain sequence. We purified recombinant D25 from the culture supernatant with Protein A.

Results

Human Peripheral Memory B-Cells Transduced with BCL6 and Bcl-xL Resemble GC-Like B-Cells We showed that overexpression of BCL6 and Bcl-xL (which are expressed in Germinal center (GC) B-cells and are under control of STAT5 (Scheeren, F. A. et al. Nat Immunol 6, 303-13 (2005); PCT/NL2008/050333)) synergize to increase the proliferative and survival potential of human memory B-cells in vitro when cultured on irradiated CD40L expressing L cells (CD40L-L cells) in the presence of IL 21. Normal human B-cells rapidly differentiate to antibody-producing plasma cells when cultured on CD40L-L cells in the presence of IL 21 (Ettinger, R. et al. J Immunol 175, 7867-79 (2005)) which is accompanied by a decrease in expression of surface BCR and MHC class II and an increase in expression of CD38 (Liu, Y. J. & Arpin, C. Immunol Rev 156, 111-26 (1997)). In contrast to non-transduced cells or cells expressing Bcl-xL only in the same culture, BCL6-only and BCL6+Bcl-xL cells both retained BCR expression and were HLA-DRhighCD38intermediate (FIG. 1a) confirming that BCL6 inhibits B-cell differentiation (Scheeren, F. A. et al. Nat Immunol 6, 303-13 (2005); Diehl, S. A. et al., J Immunol 180, 4805-15 (2008)).

BCL6+Bcl-xL positive B-cells expanded with CD40L and IL 21 express CD19, CD20, CD21 and CD22, the activation markers CD25, CD30, CD70, CD80, CD86, CD95, ICOSL, and the cytokine receptors CD132 (γc) and IL-21R. These cells express CD38 and CD20 at levels equivalent to tonsil GC cells. The expression of CD27, CXCR4, CD71, CD10 and HLA-DR on transduced cells is consistently higher compared to freshly isolated tonsil GC cells (FIG. 1a), which may be due to the activation status and increased size of the cell.

Figure 1B:
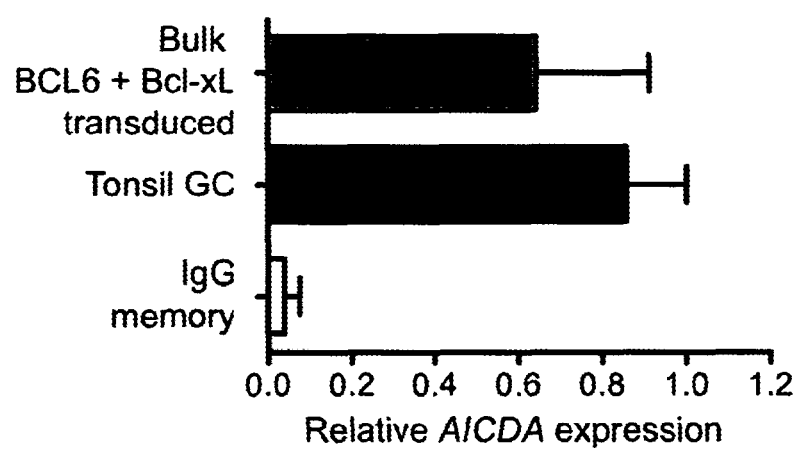

BCL6+Bcl-xL transduced cells expressed AICDA (encoding the enzyme AID) at levels comparable to those expressed by freshly isolated GC B-cells (FIG. 1b). As shown below, AID is functional in these cells as SHM in the Ig genes of the expanded B-cells were induced. Since AID is not expressed in peripheral blood memory cells (FIG. 1b) or plasma cells (Muramatsu, M. et al. J Biol Chem 274, 18470-6 (1999)), and transduced cells showed expression of typical GC cell surface markers, our results demonstrate that BCL6 and Bcl-xL expression in combination with CD40L and IL 21 signaling conferred GC-like characteristics to human $CD27^+$ memory B-cells.

Anti-RSV Antibody D25 and D25 Mutants

BCL6+Bcl-xL transduced B-cells secrete relatively high amounts of antibodies. Thereby we could select antigen-specific B-cells on the basis of secretion of specific antibody. We chose the pathogenic Respiratory Syncytial virus (RSV) as the antigenic moiety. RSV is the most common cause of bronchiolitis and pneumonia among infants and children under 1 year of age and is a serious health problem for elderly people (Thompson, W. W. et al. JAMA 289, 179-86 (2003); Hall C. B. et al NEMJ 360, 588-599 (2009)). BCL6+Bcl-xL transduced memory B-cells of a healthy donor were expanded with CD40L-L cells and IL 21 and screened for the presence of RSV-neutralizing antibodies in a microneutralization experiment (Johnson, S. et al. J Infect Dis 180, 35-40 (1999)). One of the antibodies, D25, with highest neutralizing activity was cloned by limiting dilution and further characterized (PCT/NL2008/050333). We observed median half maximum inhibitory concentrations (IC50) against the RSV-A2 virus in the range of 2.1 ng ml$^{-1}$.

Figure 2A:
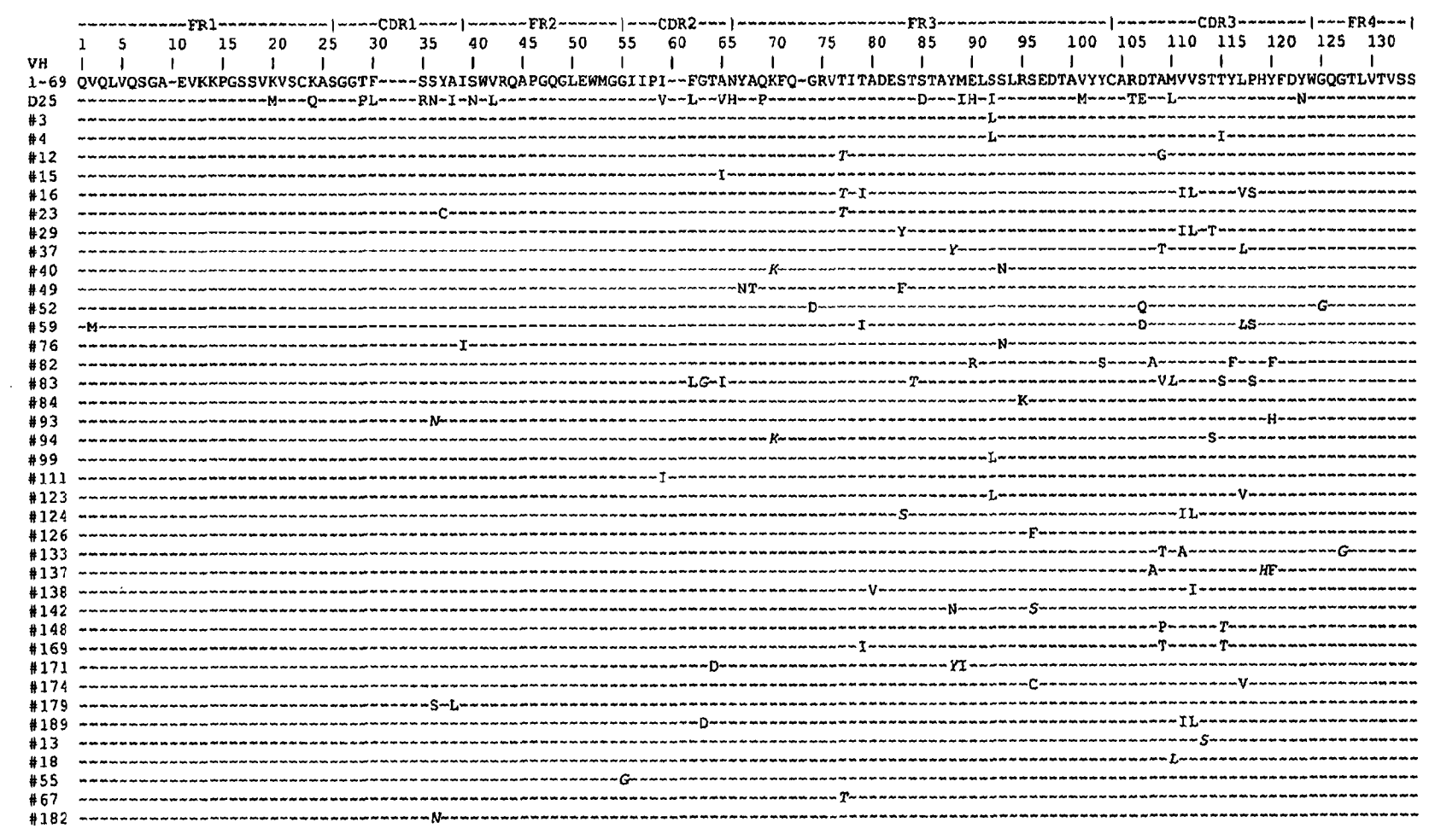
Figure 2B:
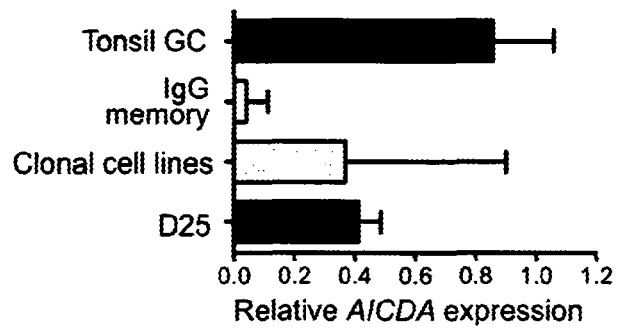
Figure 2C:
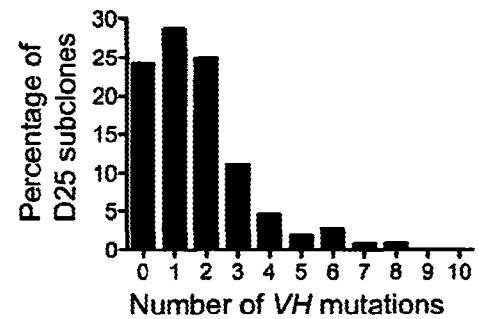
Figure 2D:
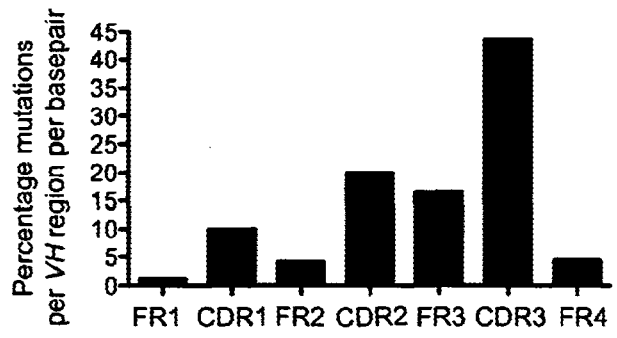

Before we studied the functional activity of AID in the D25 cell line we analyzed the AICDA expression in 23 monoclonal cell lines by real-time PCR. AID expression in these cell lines was variable. Several clones expressed levels similar to GC tonsil B-cells, whereas others were AICDA low (FIG. 2b). To determine whether AID is functional in the B-cell clones, we subcloned the RSV specific monoclonal B-cell line D25 by single cell sorting and analyzed their VH genes for the presence of mutations. Sixty three percent of the wells that were seeded with one cell showed robust expansion, showing that expression of AID does not lead to massive genetic instability leading to growth arrest and cell death. After 3 weeks culture supernatant of 108 subclones was harvested and the RNA from the cells isolated. Subsequently cDNA was generated and the VH region sequenced. Sequence analysis revealed a total of 184 VH mutations (107 unique mutations, FIG. 2a), resulting in an estimated mutation rate between $8.85 \times 10^{-5}$ and $5.14 \times 10^{-5}$ mutations per by per cell division, which is at the lower end of the estimated AID-mediated mutation rate in vivo ($10^{-3}$ to $10^{-5}$) (Peled, J. U. et al. Annu Rev Immunol 26, 481-511 (2008)). The VH genes of the individual subclones show a variable number of mutations with 65% of subclones harboring one to three mutations in their VH region (of which 23% are silent mutations) and 11% harboring more than three VH mutations. Twenty four percent of the clones had no VH mutations (FIG. 2c). The 372-basepair VH gene of D25 contains 26 AID mutational hotspots (RGYW/WRCY) that account for 30% of the total mutations. Mutations were predominantly observed in the CDR regions and FR3 (FIG. 2d).

Figure 2E:
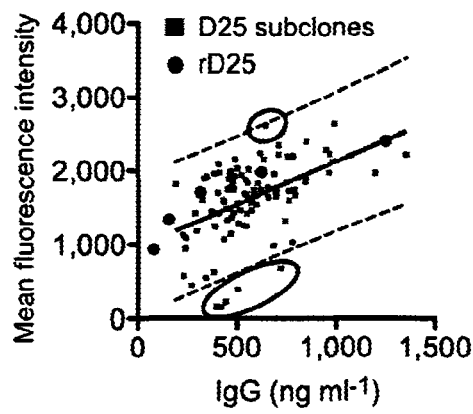

While the supernatants of the majority of D25 subclones bound to RSV-infected HEp2 cells similar to recombinant D25, some of those clones bound either less or better than D25 (FIG. 2e). The differences in binding activities were associated with mutations in the VH regions.

Regulation of AID Expression in Bcl6+Bcl-xL Transduced B Cells

Figure 3A:
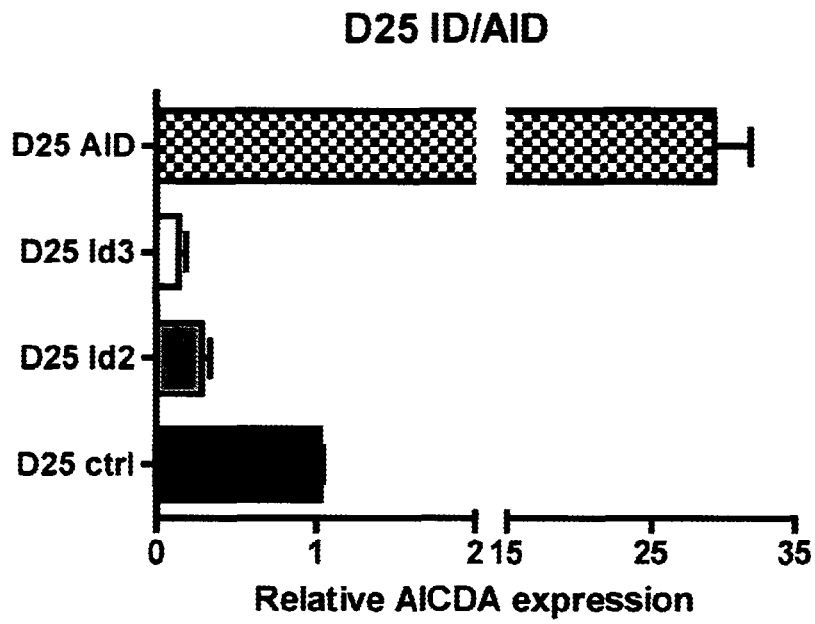
Figure 3B:
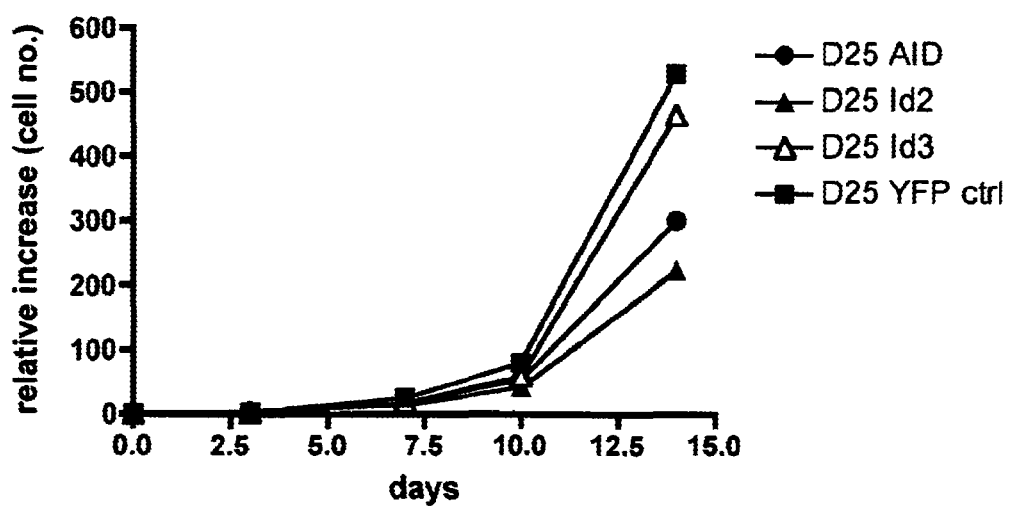
Figure 4A:
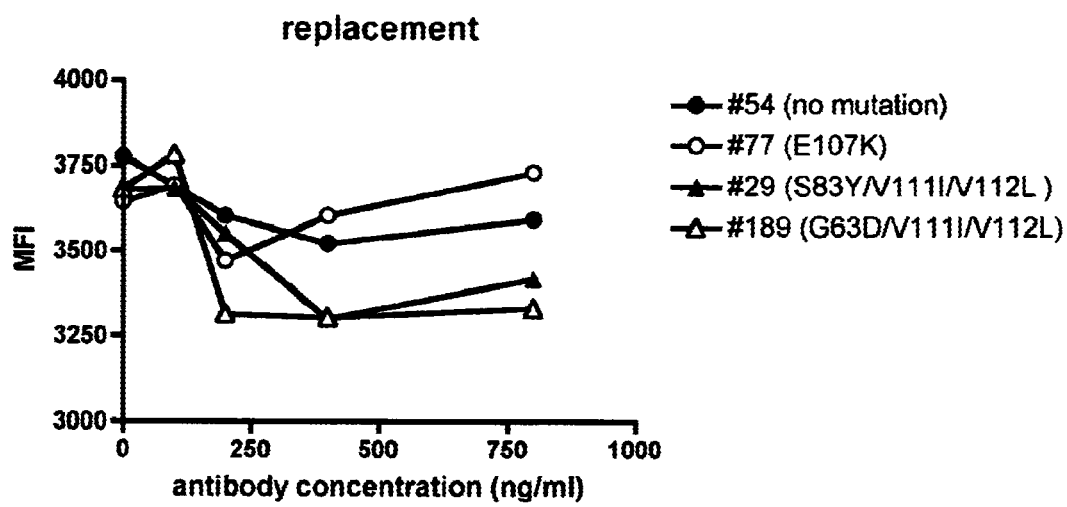
Figure 4B:
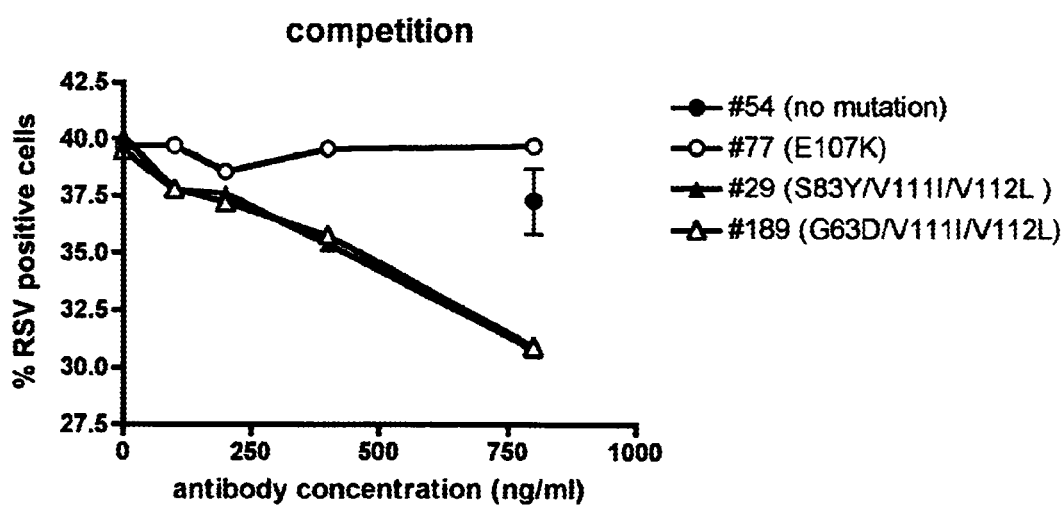

For some applications it is desirable to inhibit AID to prevent accumulation of mutations in the Ig genes of BCL6+ Bcl-xL transduced B-cell clones. To achieve this we took advantage of the fact that AID is regulated by the basic Helix Loop Helix transcription factor E47 (Sayegh, C. E., et al. Nat Immunol 4, 586-93 (2003)). We overexpressed the Helix loop Helix factor inhibitors of DNA binding ID2 and ID3 which are known to form transcriptionally inactive complexes with E47, thereby inhibiting AID expression (Sayegh, C. E., et al. Nat Immunol 4, 586-93 (2003)). As shown in FIG. 3a, overexpression of both ID2 and ID3 strongly reduced AICDA levels in the D25 cell line. Proliferation of the cell line was reduced when ID2 but not when ID3 was expressed (FIG. 3b). Overexpression of AID also reduced the proliferative capacity of the D25 cells. As expected, overexpression of AID strongly enhanced the expression of AID (FIG. 3a). Thus modulation of ID2 and/or ID3 levels provides a method to modulate AID induced mutations in BCL6+Bcl-xL transduced B-cells.

Function of D25 is Altered by Amino Acid Substitution Due to AID Activity

Figure 5:
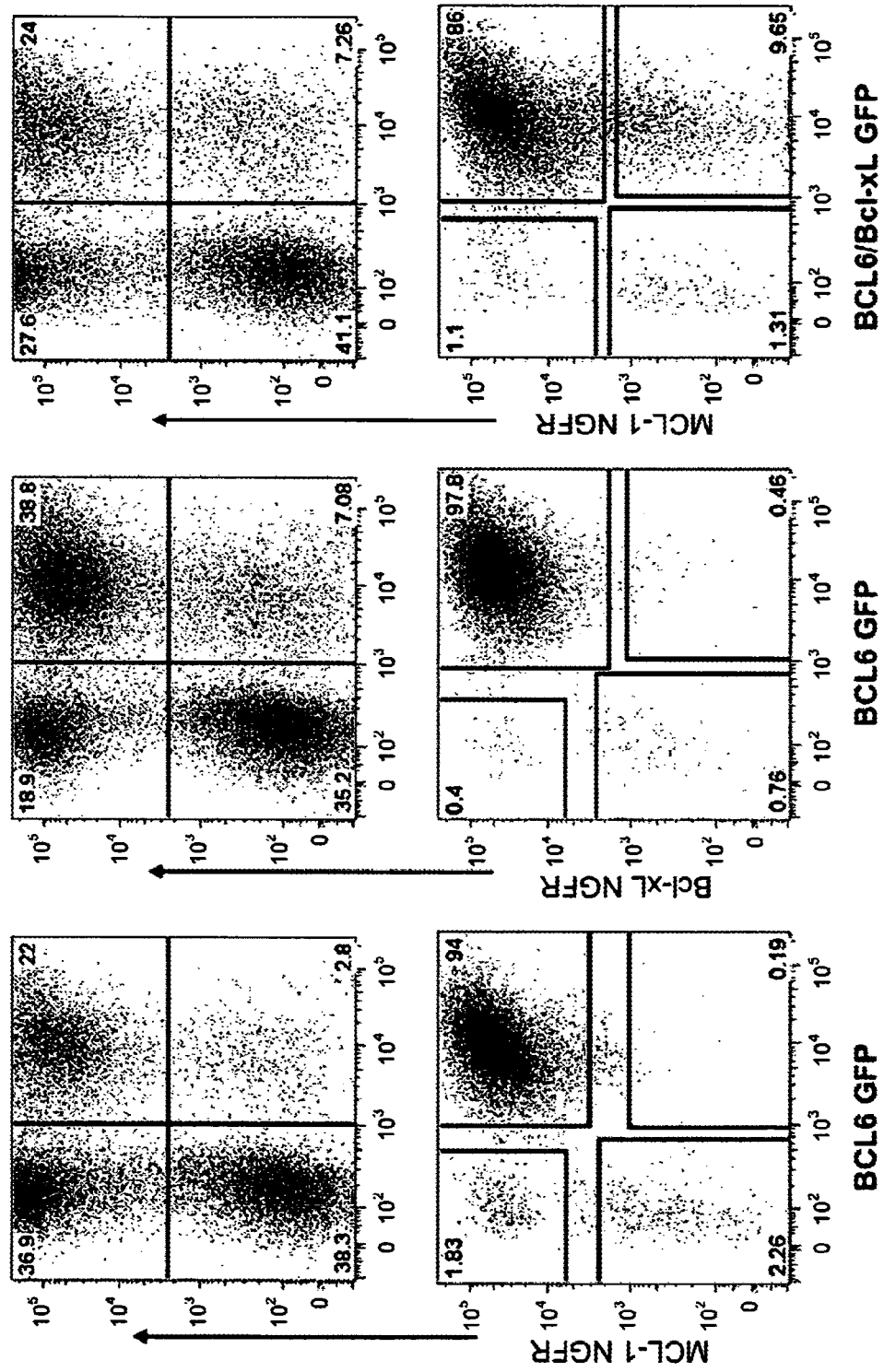
Figure 7A:
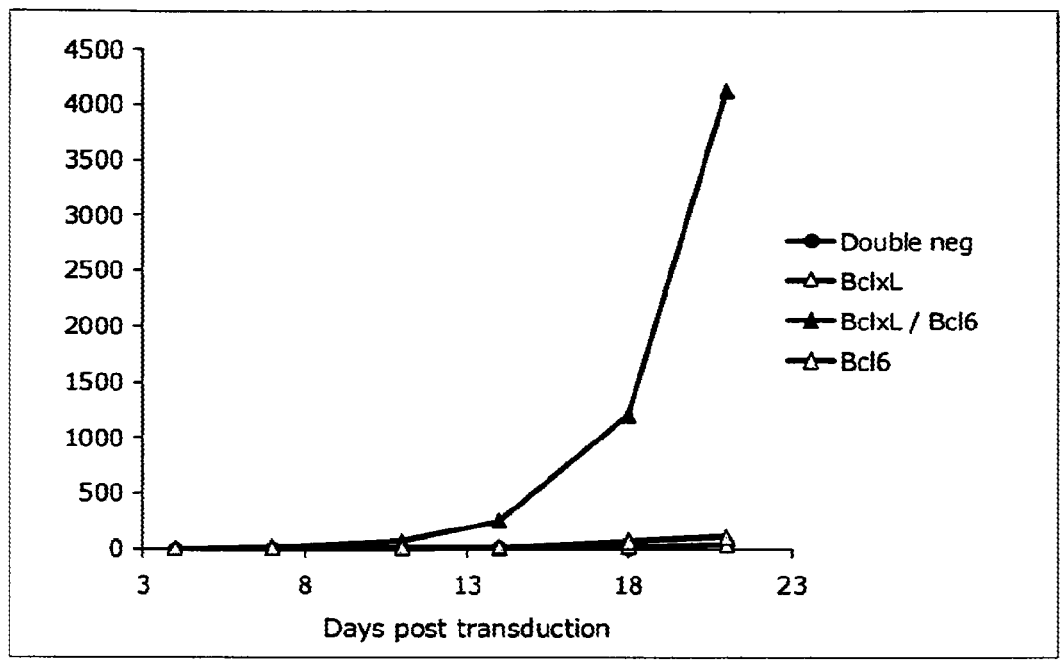
Figure 7B:
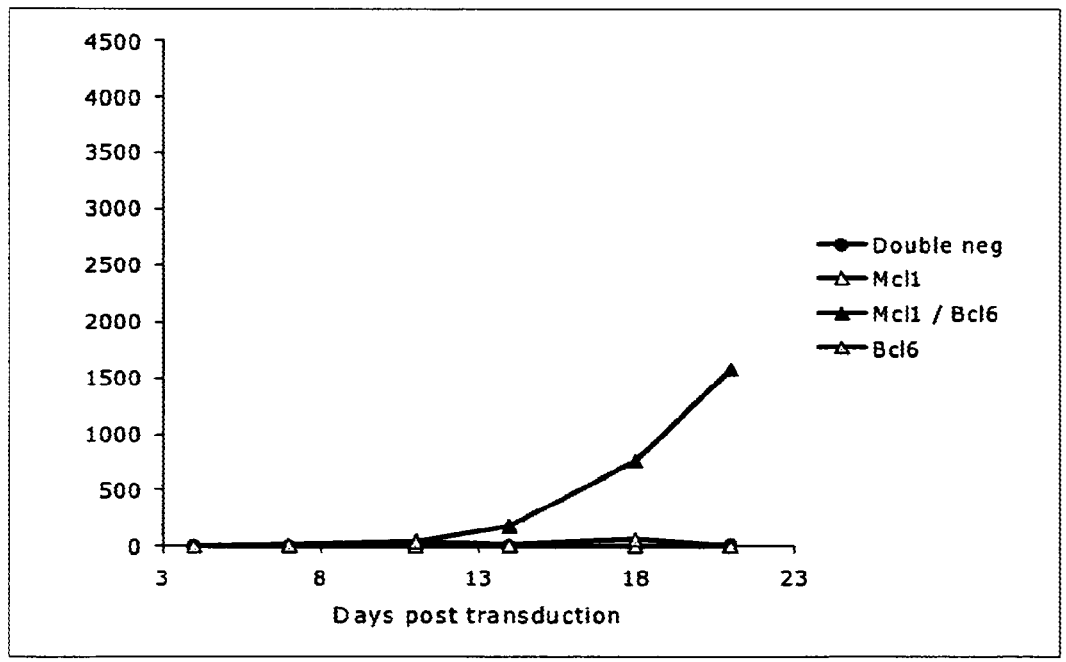
Figure 7C:
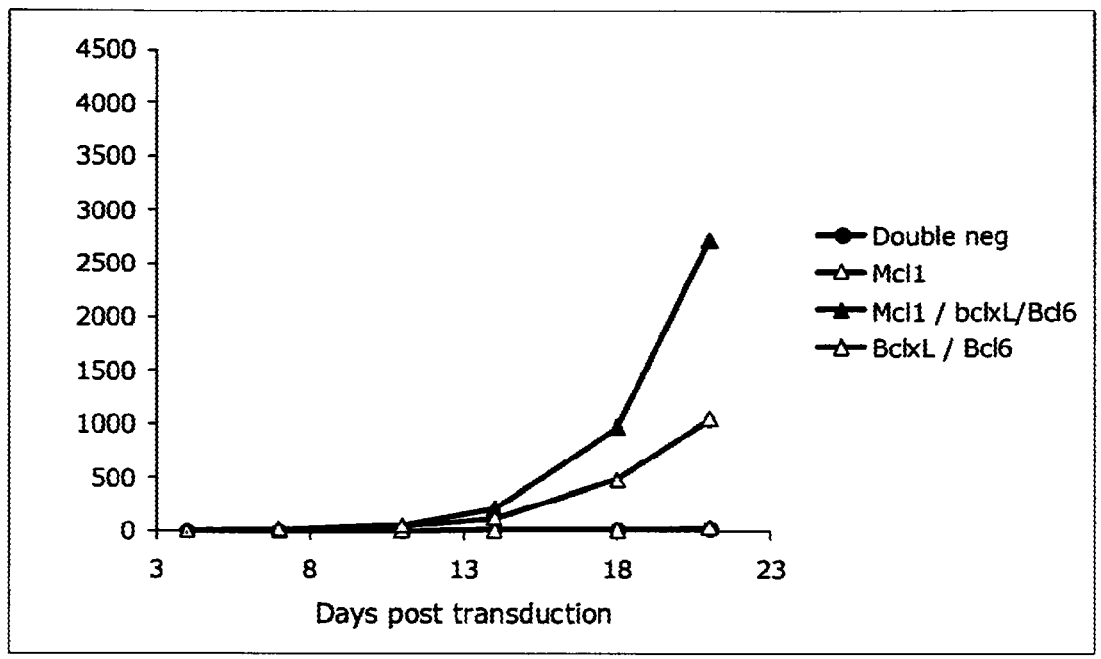
Figure 8:
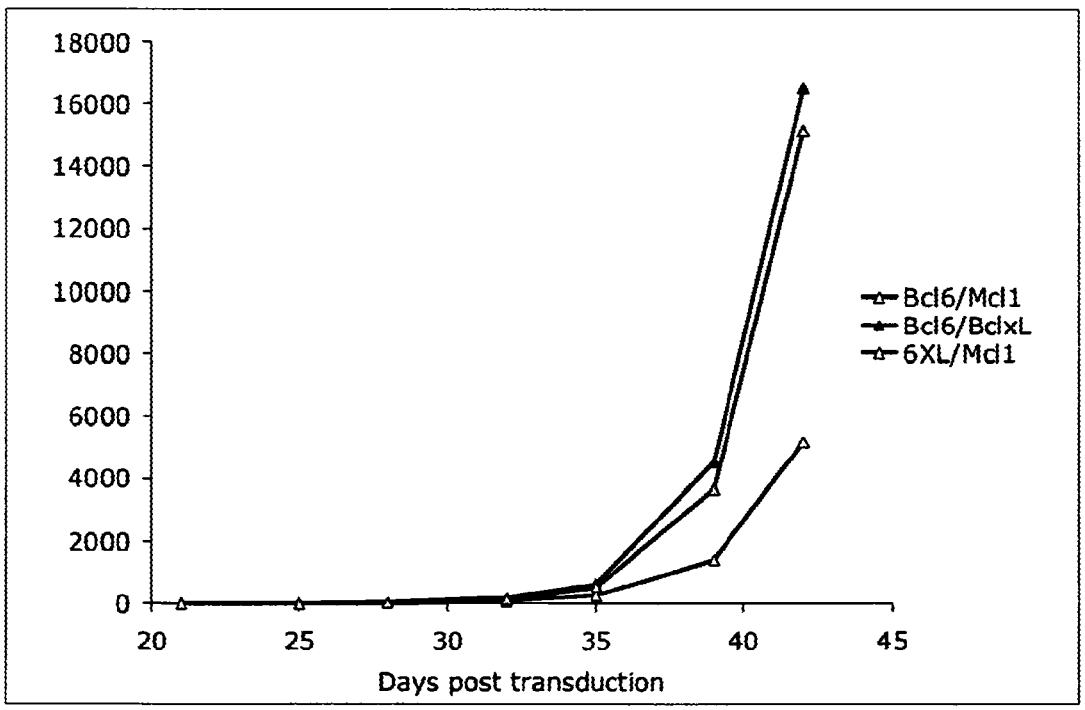
Figure 9A:
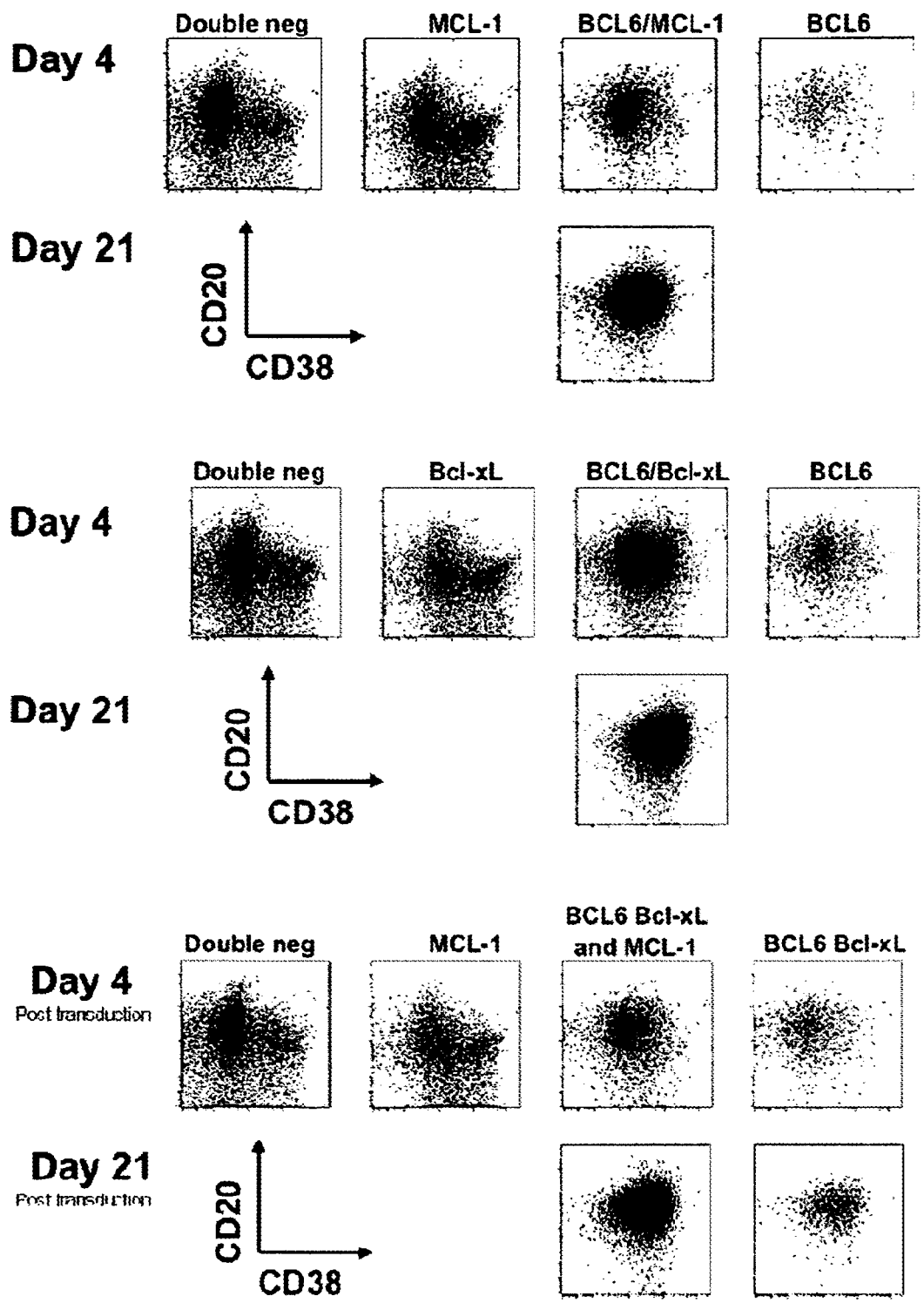
Figure 9B:
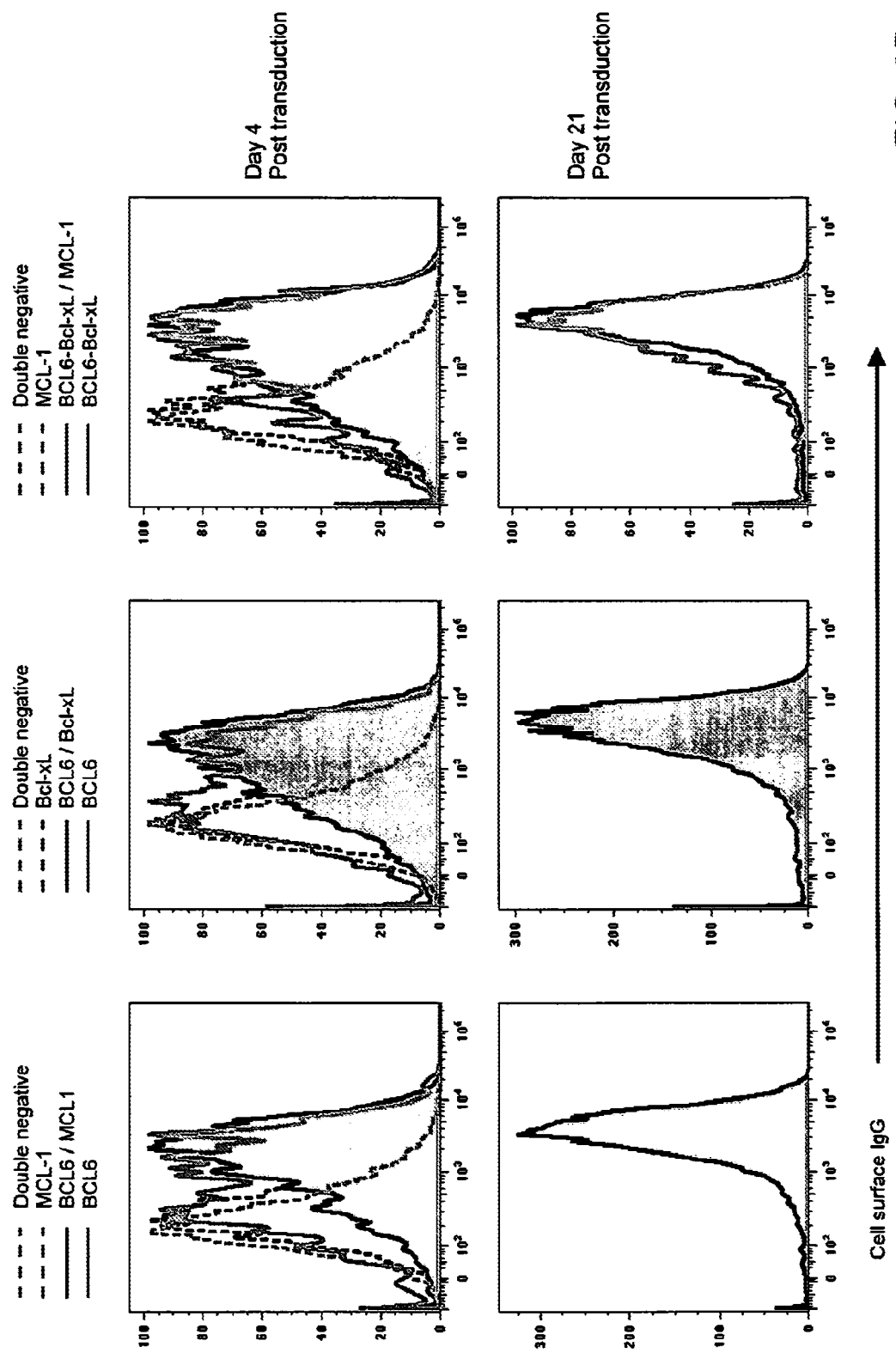

We wondered if we might find new subclones of D25 that show an altered function. However, since the affinity of D25 for it putative target, the RSV Fusion (F) protein is already high and D25 neutralizes RSV already at low concentration it was difficult to find clones that would be better then D25 itself. Nevertheless we tested the B-cell culture supernatant of the D25 subclones twice for binding to RSV infected HEp2 cells and once for competition with PE-labeled D25. These experiments gave variable results (data not shown) but when all the top 25 antibodies from each data set were compared with the VH sequences some very interesting amino acid position appeared. Several D25 subclones were produced as recombinant protein of which clone #59 still had the same configuration as the original D25 clone, #77 contained a very typical mutation at position 107 (E107K), that seem to cause a reduced binding to RSV infected HEp2 cells since other clones that lost binding to infected HEp2 cells also gathered this mutation. Furthermore clone#29 (S83Y/V111I/V112L) and #189 (G63D/V111I/V112L) share a mutation at position 111 and 112 (V→I and V→L). These two clones replace the original D25 antibody from binding to RSV infected HEp2 cells (FIG. 4*a*) in a dose dependent manner, while D25 itself and the nonbinding antibody can not replace the PE-labeled D25 antibody. In addition in a direct competition the two clones #29 and #189 again reduce the binding of the original immunoglobulin D25 (FIG. 4*b*). Thus by expression of AID in our BCL6+Bcl-xL B-cell lines we perform in vitro antibody affinity maturation within the original B-cell.

Expression of the Anti-Apoptotic Gene MCL-1 Alone or in Combination with BCL6 and/or Bcl-xL Increases Survival and Proliferation of Human B Cells Since B cell cultures with BCL6 alone and co-stimulated with CD40L and Il-21 show a block in differentiation toward plasmablasts but lack the signals for enhancing survival and proliferation, we studied besides Bcl-xL also the role of the anti-apoptotic molecule MCL-1 in this process. When activated $CD19^+CD27^+IgM^-IgA^-$ memory cells were transduced with: (i) BCL6-GFP and MCL-1-NGFR, or (ii) BCL6-GFP and Bcl-xL-NGFR or (iii) BCL6-Bcl-xL-GFP and MCL-1-NGFR (FIG. 5), they all showed enhanced survival. Cells containing BCL6 MCL-1 proliferated 3 times slower compared to cells containing BCL6 and Bcl-xL or BCL6, Bcl-xL and MCL-1 (FIGS. 6, 7 and 8). Like Bcl-xL, MCL-1 does not interfere with the function of BCL6, namely the block in differentiation towards plasmablast and these co-transduced cells indeed still posses a Germinal center phenotype (CD20+CD38+) (FIG. 9A) and also still express a surface expressed immunoglobulin (FIG. 9B). The expression of AID in MCL1 BCL6 and/or Bcl-xL transduced cells is expected not to be altered.

Regulation of AID Expression in Bcl6+Mcl-1 Transduced B Cells

As shown above for the BCL6+Bcl-xL transduced B-cell clones, ID2 and ID3 are also overexpressed in Bcl6+Mcl-1 transduced B cells, thereby inhibiting AID expression (Sayegh, C. E., et al. Nat Immunol 4, 586-93 (2003)).

Subsequently, it is demonstrated, for instance by using quantitative RT-PCR, that overexpression of both ID2 and ID3 reduce AICDA levels in these cells. Thus increasing ID2 and/or ID3 levels provides a method to prevent AID induced mutations in BCL6+Mcl-1 transduced B-cells. The procedures are described in the "Methods" section above.

REFERENCES

Adams J. M. et al. Current Opinion in Immunology 19, 488-496 (2007)
Banchereau J et al. Science 251, 70-72 (1991)
Baron, U. and Bujard, H. Methods Enzymol 327, 401-21 (2000)
Boise, L. H. et al. Cell 74, 597-608 (1993)
Chipuk, J. E. et al. Trends in Cell Biol 18, 157-163 (2007)
Christopherson, K. S. et al. PNAS 89, 6314-8 (1992)
Close, P. M., et al. J Pathol 162, 209-16 (1990)
Diehl, S. A. et al. J Immunol 180, 4805-15 (2008)
Ettinger, R. et al. J Immunol 175, 7867-79 (2005)
Good, K. L et al. J Immunol 177, 5236-47 (2006)
Gossen, M. and Bujard, H. Proc Natl Acad Sci USA 89, 5547-51 (1992)
Gossen, M. et al. Science 268, 1766-9 (1995)
Guzman, L. M. et al. Bacteriol 177, 4121-4130 (1995)
Hall C. B. et al. NEMJ 360, 588-599 (2009)
Ichikawa H. T. et al. J Immunol 177, 355-361 (2006)
Johnson, S. et al. J Infect Dis 180, 35-40 (1999)
Kee B. L. Nat Rev Immunol 9, 175-84 (2009)
Kinsella, T. M. et al Hum Gene Ther 7, 1405-1413 (1996)
Kuo, T. C. et al. J Exp Med 204, 819-830 (2007)
Liu, Y. J. & Arpin, C. Immunol Rev 156, 111-26 (1997)
Maurer, U. et al. Mol Cell 21, 749-760 (2006)
Muramatsu, M. et al. J Biol Chem 274, 18470-6 (1999)
Peled, J. U. et al. Annu Rev Immunol 26, 481-511 (2008)
Rousset F et al. PNAS 89, 1890-1893 (1992)
Sayegh, C. E., et al. Nat Immunol 4, 586-93 (2003)
Scheeren, F. A. et al. Nat Immunol 6, 303-13 (2005)
Sidwell, R. W. & Barnard, D. L. Antiviral Res 71, 379-90 (2006)
Smit, L. A. et al. Cancer Res 63, 3894-8 (2003)
Spits H. et al. J Exp Med 192, 1775-83 (2000)
Tan S et al. PNAS 100, 11997-12002 (2003)
Thompson, W. W. et al. JAMA 289, 179-86 (2003)
Zamore et al. Cell 101, 25-33 (2000)

The invention claimed is:

1. A method for increasing the occurrence of somatic hypermutations in an antibody producing plasmablast-like B-cell, the method comprising:
    introducing an exogenous nucleic acid molecule encoding Bcl-6 into a B cell, wherein said B cell is a memory B cell, and introducing an exogenous anti-apoptotic nucleic acid molecule into said B cell, thus generating an antibody producing plasmablast-like B-cell with functional AID activity; and
    demonstrating an increased incidence of somatic hypermutations resulting from said functional AID activity.

2. The method according to claim 1, wherein said anti-apoptotic nucleic acid molecule comprises a BCL2 family gene.

3. The method according to claim 1, further comprising: providing said B-cell with IL21 and CD40L.

4. The method according to claim 2, wherein the BCL2 family gene is Bcl-xL or Mcl 1.

5. The method according to claim 1, wherein the increased incidence of somatic hypermutations is demonstrated by analyzing the VH gene of said B cell for the presence of mutations.

6. A method according to claim 5, further comprising: analyzing the VH and VL sequences of said B cell or said antibody to determine the immunoglobulin residues important for antigen binding.

7. The method according to claim 5, further comprising at least one of:
    selecting immunoglobulins that harbor mutations that were not present in the B cell before transduction with Bcl-6 and the anti-apoptotic nucleic acid;
    selecting one or more immunoglobulin variants having a higher affinity for a ligand that is recognized by the immunoglobulin, or
    selecting a variant that is more stable than other variants.

* * * * *